US011135294B2

(12) United States Patent
Oldham et al.

(10) Patent No.: US 11,135,294 B2
(45) Date of Patent: Oct. 5, 2021

(54) METHODS FOR RADIOTHERAPY TO TRIGGER LIGHT ACTIVATION DRUGS

(71) Applicants: IMMUNOLIGHT, LLC, Detroit, MI (US); DUKE UNIVERSITY, Durham, NC (US)

(72) Inventors: Mark Oldham, Durham, NC (US); Justus Adamson, Durham, NC (US); Mark W. Dewhirst, Durham, NC (US); Paul Yoon, Durham, NC (US); Harold Walder, Belville, NC (US); Frederic A. Bourke, Jr., Greenwich, CT (US); Zakaryae Fathi, Raleigh, NC (US); Wayne F. Beyer, Jr., Bahama, NC (US)

(73) Assignees: IMMUNOLIGHT, LLC, Detroit, MI (US); DUKE UNIVERSITY, Durham, NC (US)

( * ) Notice: Subject to any disclaimer, the term of this patent is extended or adjusted under 35 U.S.C. 154(b) by 463 days.

(21) Appl. No.: 15/770,926

(22) PCT Filed: Oct. 26, 2016

(86) PCT No.: PCT/US2016/058868
§ 371 (c)(1),
(2) Date: Apr. 25, 2018

(87) PCT Pub. No.: WO2017/075057
PCT Pub. Date: May 4, 2017

(65) Prior Publication Data
US 2018/0311355 A1    Nov. 1, 2018

Related U.S. Application Data

(60) Provisional application No. 62/326,176, filed on Apr. 22, 2016, provisional application No. 62/246,360, filed on Oct. 26, 2015.

(51) Int. Cl.
*A61K 41/00*    (2020.01)
*A61K 31/409*    (2006.01)
(Continued)

(52) U.S. Cl.
CPC ........ *A61K 41/0066* (2013.01); *A61K 31/352* (2013.01); *A61K 31/403* (2013.01);
(Continued)

(58) Field of Classification Search
CPC .............. A61K 41/0066; A61K 31/352; A61K 31/403; A61K 31/409; A61K 31/525;
(Continued)

(56) References Cited

U.S. PATENT DOCUMENTS

2004/0238740 A1*  12/2004  Kohama ................. H01J 37/28
                                                          250/310
2014/0114150 A1*   4/2014  Pogue ....................... G01T 1/22
                                                          600/317

FOREIGN PATENT DOCUMENTS

WO    WO 2015/183346 A2    12/2015

OTHER PUBLICATIONS

International Search Report and Written Opinion dated Jan. 3, 2017, in PCT/US2016/058868, filed Oct. 26, 2016.
(Continued)

*Primary Examiner* — Phillip A Gray
(74) *Attorney, Agent, or Firm* — Oblon, McClelland, Maier & Neustadt, L.L.P.

(57) ABSTRACT

A method and system for treating a subject with a disorder which provides within the subject at least one photoactivatable drug for treatment of the subject, applies initiation energy from at least one source to generate inside the subject a preferential x-ray flux for generation of Cherenkov radiation (CR) light capable of activating at least one photoactivatable drug, and from the CR light, activating inside the
(Continued)

subject the at least one photoactivatable drug to thereby treat the disorder.

100 Claims, 11 Drawing Sheets

(51) Int. Cl.
| | |
|---|---|
| *A61N 5/06* | (2006.01) |
| *A61K 31/655* | (2006.01) |
| *A61K 33/02* | (2006.01) |
| *A61K 31/525* | (2006.01) |
| *A61K 31/352* | (2006.01) |
| *A61K 31/403* | (2006.01) |
| *A61K 33/24* | (2019.01) |
| *A61N 5/10* | (2006.01) |
| *A61K 31/426* | (2006.01) |
| *A61K 31/47* | (2006.01) |
| *B82Y 5/00* | (2011.01) |

(52) U.S. Cl.
CPC .......... *A61K 31/409* (2013.01); *A61K 31/525* (2013.01); *A61K 31/655* (2013.01); *A61K 33/02* (2013.01); *A61K 33/24* (2013.01); *A61N 5/062* (2013.01); *A61N 5/0624* (2013.01); *A61N 5/10* (2013.01); *A61K 31/426* (2013.01); *A61K 31/47* (2013.01); *A61K 2300/00* (2013.01); *A61N 2005/065* (2013.01); *A61N 2005/1095* (2013.01); *A61N 2005/1098* (2013.01); *B82Y 5/00* (2013.01); *Y02A 50/30* (2018.01)

(58) Field of Classification Search
CPC ...... A61K 31/655; A61K 33/02; A61K 33/24; A61N 5/062; A61N 5/0624; A61N 5/10
USPC .................................................. 604/20, 500
See application file for complete search history.

(56) References Cited

OTHER PUBLICATIONS

Axelsson, J. et al., "Cerenkov emission induced by external beam radiation stimulates molecular fluorescence", Medical Physics, vol. 38, No. 7, Jul. 2011, p. 4127-4132.

\* cited by examiner

METHODS FOR RADIOTHERAPY TO TRIGGER LIGHT ACTIVATION DRUGS

CROSS REFERENCE TO RELATED APPLICATIONS

This application is related to U.S. provisional Ser. No. 61/982,585, filed Apr. 22, 2014, entitled "INTERIOR ENERGY-ACTIVATION OF PHOTO-REACTIVE SPECIES INSIDE A MEDIUM OR BODY USING AN X-RAY SOURCE EMITTING LOW ENERGY X-RAYS AS INITIATION ENERGY SOURCE", the entire contents of which are hereby incorporated by references. This application is related to provisional Ser. No. 62/096,773, filed: Dec. 24, 2014, entitled "INTERIOR ENERGY-ACTIVATION OF PHOTO-REACTIVE SPECIES INSIDE A MEDIUM OR BODY USING AN X-RAY SOURCE EMITTING LOW ENERGY X-RAYS AS INITIATION ENERGY SOURCE," the entire contents of each of which is incorporated herein by reference. This application is related to U.S. provisional Ser. No. 62/132,270, filed Mar. 12, 2015, entitled "TUMOR IMAGING WITH X-RAYS AND OTHER HIGH ENERGY SOURCES USING AS CONTRAST AGENTS PHOTON-EMITTING PHOSPHORS HAVING THERAPEUTIC PROPERTIES", the entire contents of which are hereby incorporated by references. This application is related to U.S. provisional Ser. No. 62/147,390, filed Apr. 14, 2015, entitled "TUMOR IMAGING WITH X-RAYS AND OTHER HIGH ENERGY SOURCES USING AS CONTRAST AGENTS PHOTON-EMITTING PHOSPHORS HAVING THERAPEUTIC PROPERTIES", the entire contents of which are hereby incorporated by references.

This application is related to non-provisional U.S. Ser. No. 12/401,478 (now U.S. Pat. No. 8,376,013) entitled "PLASMONIC ASSISTED SYSTEMS AND METHODS FOR INTERIOR ENERGY-ACTIVATION FROM AN EXTERIOR SOURCE, filed Mar. 10, 2009, the entire contents of which are incorporated herein by reference. This application is related to provisional Ser. No. 61/035,559, filed Mar. 11, 2008, entitled "SYSTEMS AND METHODS FOR INTERIOR ENERGY-ACTIVATION FROM AN EXTERIOR SOURCE," the entire contents of which are hereby incorporated herein by reference. This application is related to provisional Ser. No. 61/030,437, filed Feb. 21, 2008, entitled "METHODS AND SYSTEMS FOR TREATING CELL PROLIFERATION DISORDERS USING PLASMONICS ENHANCED PHOTOSPECTRAL THERAPY (PEPST) AND EXCITON-PLASMON ENHANCED PHOTOTHERAPY (EPEP)," the entire contents of which are hereby incorporated herein by reference. This application is related to non-provisional Ser. No. 12/389,946, filed Feb. 20, 2009, entitled "METHODS AND SYSTEMS FOR TREATING CELL PROLIFERATION DISORDERS USING PLASMONICS ENHANCED PHOTOSPECTRAL THERAPY (PEPST) AND EXCITON-PLASMON ENHANCED PHOTOTHERAPY (EPEP)," the entire contents of which are hereby incorporated herein by reference. This application is related to non-provisional Ser. No. 11/935,655, filed Nov. 6, 2007, entitled "METHODS AND SYSTEMS FOR TREATING CELL PROLIFERATION RELATED DISORDERS," and to provisional Ser. No. 60/910,663, filed Apr. 8, 2007, entitled "METHOD OF TREATING CELL PROLIFERATION DISORDERS," the contents of each of which are hereby incorporated by reference in their entireties. This application is related to provisional Ser. No. 61/035,559, filed Mar. 11, 2008, entitled "SYSTEMS AND METHODS FOR INTERIOR ENERGY-ACTIVATION FROM AN EXTERIOR SOURCE," the entire contents of which are hereby incorporated herein by reference. This application is also related to provisional Ser. No. 61/792,125, filed Mar. 15, 2013, entitled "INTERIOR ENERGY-ACTIVATION OF PHOTO-REACTIVE SPECIES INSIDE A MEDIUM OR BODY," the entire contents of which are hereby incorporated herein by reference. This application is further related to provisional Ser. No. 61/505,849 filed Jul. 8, 2011, and U.S. application Ser. No. 14/131,564, filed Jan. 8, 2014, each entitled "PHOSPHORS AND SCINTILLATORS FOR LIGHT STIMULATION WITHIN A MEDIUM," the entire contents of each of which is incorporated herein by reference. This application is related to and U.S. application Ser. No. 14/206,337, filed Mar. 12, 2014, entitled "INTERIOR ENERGY-ACTIVATION OF PHOTO-REACTIVE SPECIES INSIDE A MEDIUM OR BODY," the entire contents of which are hereby incorporated herein by reference. This application is related to PCT application PCT/2015/027058 filed Apr. 22, 2015 entitled "TUMOR IMAGING WITH X-RAYS AND OTHER HIGH ENERGY SOURCES USING AS CONTRAST AGENTS PHOTON-EMITTING PHOSPHORS HAVING THERAPEUTIC PROPERTIES," the entire contents of which are hereby incorporated by reference. This application is related to PCT application PCT/2015/027060 filed Apr. 22, 2015 entitled "INTERIOR ENERGY-ACTIVATION OF PHOTO-REACTIVE SPECIES INSIDE A MEDIUM OR BODY USING AN X-RAY SOURCE EMITTING LOW ENERGY X-RAYS AS INITIATION ENERGY SOURCE," the entire contents of which are hereby incorporated by reference. This application is related to U.S. provisional patent application 62/103,409 entitled "NON-INVASIVE SYSTEMS AND METHODS FOR TREATMENT OF A HOST CARRYING A VIRUS WITH PHOTOACTIVATABLE DRUGS," filed Jan. 14, 2015, 2015, the entire contents of which are hereby incorporated by reference.

This application is related to and claims priority to U.S. provisional patent application 62/246,360 entitled "METHODS FOR RADIOTHERAPY TO TRIGGER LIGHT ACTIVATION DRUGS," filed Oct. 26, 2015, the entire contents of which are hereby incorporated by reference. This application is related to and claims priority to U.S. provisional patent application 62/326,176 entitled "METHODS FOR RADIOTHERAPY TO TRIGGER LIGHT ACTIVATION DRUGS," filed Apr. 22, 2016, the entire contents of which are hereby incorporated by reference.

BACKGROUND OF THE INVENTION

Field of the Invention

The present invention is related to methods and systems for treating a disorder or condition in a subject.

Description of the Related Art

Cherenkov Radiation

Using radiotherapy to trigger light activated drugs has much potential for the treatment of many diseases, such as cancer. At present, Cherenkov drug activation using radioactive tracers (PET tracers such as 2-deoxy-2-[(18)F]fluoro-D-glucose ((18) (FDG), as an alternative light source for photoactivation is known. $^{18}$F-FDG is a modified glucose molecule which accumulates at sites of upregulated metabolism, delineating proliferating and inflammed regions. These radioactive tracers have been used to photoactivate caged luciferin in a breast cancer animal model expressing luciferase However, this approach was limited by the low Cherenkov light intensity from the PET radioactive traces. Models have estimated that the number of visible wavelength photons generated by $^{18}F$ in a typical $^{18}F$-FDG rodent acquisition (using 100 µCi) would be several million photons per second, orders of magnitude lower than that of a typical bioluminescent study. For imaging application, this short coming can be partly compensated through the lack of a non-specific background signal and by extending the time needed to capture greater numbers of photons for imaging purposes. Indeed, while useful for imaging, the use of the radioactive tracers exposes the subject to prolonged radiation.

Cherenkov radiation (CR) is produced when charged particles travel through a dielectric medium faster than the speed of light in that medium. First described in detail nearly 100 years ago, CR has recently been applied for biomedical imaging purposes. The first observation of CR is believed to be an account from Dr. Curie over a century ago. Pavel A. Cherenkov later characterized the phenomenon. Cherenkov radiation is polarized and continuous with an intensity distribution that is inversely proportional to the square of the wavelength. The majority of the light is in the ultraviolet (UV) and blue end of the visible spectrum.

In general, charged particles released upon radioactive decay may include electrons (such as β-particles, Auger electrons and conversion electrons), positrons (β+), and α-particles. As these particles travel, the charged particles lose energy through interactions with the surrounding matter. In the biological context this matter is mostly water. At speeds below the speed of light in water, the randomly oriented polar water molecules will align with the passing of the charged particle. After the particle passes, these aligned water molecules along this path will relax back to a lowest energy state. In cases, when the particle is traveling at super-relativistic phase velocities (i.e. the particle travels faster than the speed of light in a particular), the polarized molecules relax by releasing energy in the form of visible radiation luminescence.

Indeed, workers have used linear accelerators for external beam irradiation in a clinical setting for the delivery of high doses of shaped electron and photon beams. At sufficient energy, externally impinging electrons are capable of producing Cherenkov radiation. Detectable levels of light were reported as generated in a solid phantom, and the amount of light produced increased linearly with beam energy (up to 18 MeV), to a fluence rate of approximately 1.1 µW/cm². Even with higher fluences being obtained at around 1 µW/cm², this fluence rate is still relatively low. For imaging, fluorophores have been used to turn the broad spectrum of the CR into distinct blue and red emissions.

Psoralens and Related Compounds

The following background discussions describe the conventional understanding of 1) psoralens and their photoreactivity and 2) alkylating agents and their photoreactivity. The present invention can utilize those and other pathways to cause reactions of the photoreactive drugs with target cells.

U.S. Pat. No. 6,235,508 describes that psoralens are naturally occurring compounds which have been used therapeutically for millennia in Asia and Africa. The action of psoralens and light has been used to treat vitiligo and psoriasis (PUVA therapy; Psoralen Ultra Violet A). Psoralen is capable of binding to nucleic acid double helices by intercalation between base pairs; adenine, guanine, cytosine and thymine (DNA) or uracil (RNA). Upon sequential absorption of two UV-A photons, psoralen in its excited state reacts with a thymine or uracil double bond and covalently attaches to both strands of a nucleic acid helix. The cross-linking reaction appears to be specific for a thymine (DNA) or a uracil (RNA) base. Binding may proceed when psoralen is intercalated in a site containing thymine or uracil, but an initial photoadduct must absorb a second UVA photon to react with a second thymine or uracil on the opposing strand of the double helix in order to crosslink each of the two strands of the double helix, as shown below. This is a sequential absorption of two single photons as shown, as opposed to simultaneous absorption of two or more photons.

U.S. Pat. No. 4,748,120 of Wiesehan is an example of the use of certain substituted psoralens by a photochemical decontamination process for the treatment of blood or blood products.

Additives, such as antioxidants are sometimes used with psoralens, such as 8-MOP, AMT and I-IMT, to scavenge singlet oxygen and other highly reactive oxygen species formed during photoactivation of the psoralens. It is well known that UV activation creates such reactive oxygen species, which are capable of seriously damaging otherwise healthy cells Much of the viral deactivation may be the result of these reactive oxygen species rather than any effect of photoactivation of psoralens.

Some of the best known photoactivatable compounds are derivatives of psoralen or coumarin, which are nucleic acid intercalators. For psoralens and coumarins, this chemical pathway is likely to lead to the formation of a variety of ring-opened species, such as shown below for coumarin:

Coumarin

X = Br
R = OCH$_2$CH$_2$CH$_2$NEt$_3^+$Br$^-$

X$^1$ = H or Br

Midden (W. R. Midden, Psoralen DNA photobiology, Vol II (ed. F. P. Gaspalloco) CRC press, pp. 1. (1988) has presented evidence that psoralens photoreact with unsaturated lipids and photoreact with molecular oxygen to produce active oxygen species such as superoxide and singlet oxygen that cause lethal damage to membranes.

U.S. Pat. No. 6,235,508 describes that 8-MOP and AMT are unacceptable photosensitizers, because each indiscriminately damages both cells and viruses. Studies of the effects of cationic side chains on furocoumarins as photosensitizers are reviewed in Psoralen DNA Photobiology, Vol. I, ed. F. Gaspano, CRC Press, Inc., Boca Raton, Fla., Chapter 2. U.S. Pat. No. 6,235,508 gleans the following from this review: most of the amino compounds had a much lower ability to both bind and form crosslinks to DNA compared to 8-MOP, suggesting that the primary amino functionality is the preferred ionic species for both photobinding and crosslinking.

U.S. Pat. No. 5,216,176 describes a large number of psoralens and coumarins that have some effectiveness as photoactivated inhibitors of epidermal growth factor. Halogens and amines are included among the vast functionalities that could be included in the psoralen/coumarin backbone. This reference is incorporated herein by reference in its entirety.

U.S. Pat. No. 5,984,887 describes using extracorporeal photopheresis with 8-MOP to treat blood infected with CMV. The treated cells as well as killed and/or attenuated virus, peptides, native subunits of the virus itself (which are released upon cell break-up and/or shed into the blood) and/or pathogenic noninfectious viruses are then used to generate an immune response against the virus, which was not present prior to the treatment.

Other Photoactive Compounds

Other photoactive or photoactivatable compounds are known in the art. Of these, an article by Warfield et al entitled "Ebola Virus Inactivation with Preservation of Antigenic and Structural Integrity by a Photoinduable Alkylating Agent," J. Infect. Dis. 2007 Nov. 15; 196 Suppl 2:S276-83 describes the treatment of the Zaire Ebola virus (ZEBOV) ex situ by extraction of infected blood from a mouse and exposure of the extracted blood to UV light (310 to 360 nm) with the blood containing an alkylating agent, in this case iodonophthylazide (INA) to inactivate the ZEBOV. Mice treated with the inactivated Ebola virus were resistant to exposure to the Ebola virus. These authors reported that INA is hydrophobic compound that preferentially partitions into lipid bilayers of the Ebola virus. These authors reported that the "INA treatment renders ZEBOV completely noninfectious without structural perturbation" and that "INA-inactivated ZEBOV was immunogenic and protected mice from lethal challenge."

U.S. Pat. No. 7,049,110 entitled "Inactivation of West Nile virus and malaria using photosensitizers" describes the inactivation of microorganisms in fluids or on surfaces, preferably the fluids that contain blood or blood products and biologically active proteins. An effective, non-toxic amount of a photosensitizer was added to the fluid, and the fluid was exposed to photoradiation sufficient to activate the photosensitizer whereby microorganisms were inactivated.

The '110 patent describes a 7,8-dimethyl-10-ribityl isoalloxazine photosensitizers and other photosensitizers including endogenous alloxazine or isoalloxazine photosensitizers. The '110 patent describes the treatment of a host carrying various microorganisms including viruses (both extracellular and intracellular), bacteria, bacteriophages, fungi, blood-transmitted parasites such as malaria, and protozoa. Exemplary viruses include acquired immunodeficiency (HIV) virus, hepatitis A, B and C viruses, sinbis virus, cytomegaloviris, vesicular stomatitis virus, herpes simplex viruses, e.g. types I and II, human T-lymphotropic retroviruses, HTLV-III, lymphadenopathy virus LAV/IDAV, parvovirus, transfusion-transmitted (TT) virus, Epstein-Barr virus, West Nile virus and others known to the art. Bacteriophages include ΦX174, Φ6, λ, R17, T4, and T2. Exemplary bacteria include *P. aeruginosa, S. aureus, S. epidermis, L. monocytogenes, E. coli, K. pneumonia* and *S. marcescens*. One particular class of microorganisms is non-screened microorganisms—those microorganisms that are not screened by current blood banking processes. Some non-screened microorganisms include malaria and West Nile virus. One class of microorganisms includes those transmitted by mosquitoes, including malaria and West Nile virus.

The '110 patent describes that the preferable use endogenous photosensitizers, including endogenous photosensitizers which function by interfering with nucleic acid replication. In 7,8-dimethyl-10-ribityl isoalloxazine, the chemistry believed to occur between 7,8-dimethyl-10-ribityl isoalloxazine and nucleic acids does not proceed via singlet oxygen-dependent processes (i.e. Type II mechanism), but rather by direct sensitizer-substrate interactions (Type I mechanisms). In addition, 7,8-dimethyl-10-ribityl isoalloxazine appears not to produce large quantities of singlet oxygen upon exposure to UV light, but rather exerts its effects through direct interactions with substrate (e.g., nucleic acids) through electron transfer reactions with excited state sensitizer species.

An article by Sharma et al. entitled "Safety and protective efficacy of INA-inactivated Venezuelan equine encephalitis virus: Implication in vaccine development," in Vaccine, volume 29, issue 5, 29 Jan. 2011, pages 953-959, described that that hydrophobic alkylating compound, 1,5-iodonaphthyl-azide (INA) can efficiently inactivate the virulent strain of Venezuelan equine encephalitis virus (VEEV), upon exposure of the INA to "full light conditions." Sharma et al. further demonstrated the protective efficacy of INA-inactivated V3000 and V3526 to not cause disease in suckling mice and to induce an anti-VEEV antibody response which protected mice from a virulent VEEV challenge. Sharma et al. reported that none of the mice which received INA-inactivated V3526 showed any clinical symptoms of disease such as, hunched posture, stunted growth, lethargic or paralysis and grew similar to that of the control mice.

An article by Heilman et al. entitled "Light-Triggered Eradication of *Acinetobacter baumannii* by Means of NO Delivery from a Porous Material with an Entrapped Metal Nitrosyl" in J. Am. Chem. Soc., 2012, 134 (28), pp 11573-11582 (May 11, 2012) describes photoactive manganese nitrosyl, namely [Mn(PaPy3)(NO)](C104) ({Mn—NO}), loaded into the columnar pores of an MCM-41 host. Heliman et al. report that, when suspensions of the loaded materials in saline solution were exposed to low-power (10-100 mW) visible light, rapid release of NO was observed. The released nitric oxide effectively cleared the bacteria from the treated areas of the plates, showing that the nitric oxide easily penetrated through the agar layer. The amount of light used to activate the compound was 100 milliWatts per square centimeter.

U.S. Pat. No. 8,268,602 entitled "CELLUAR AND VIRAL INACTIVATION" describes procedures for providing compositions of inactivated viruses, bacteria, fungi, parasites and tumor cells that can be used as vaccines, as well as methods for making such inactivated viruses, bacteria, fungi, parasites and tumor cells are also provided. More specifically, the '602 patent describes methods for inactivating an infective agent or cancer cell that involve exposing the agent or cell to a hydrophobic photoactivatable compound, for example, 1,5-iodonaphthylazide (INA) activated by ultraviolet light.

The above-noted patents, patent applications, and articles are incorporated by reference in their entirety herein. The following patents, patent applications, and articles are also incorporated by reference in their entirety herein.

SUMMARY OF THE INVENTION

The present disclosure relates to the use of Cherenkov radiation (CR) to trigger light activation drugs inside a patient or subject. The methods and systems of the present disclosure do not need or rely on light from radioactive traces to trigger light activation drugs. The methods described herein exploit the energy deposition properties of high energy X-rays, generated for example by linear accelerators to generate light inside the subject being treated and to thereby activate drugs in vivo.

In one embodiment of the present invention, there is provided a method for treating a subject with a disorder which provides within the subject at least one photoactivatable drug for treatment of the subject, applies initiation energy from at least one source to generate inside the subject a preferential x-ray flux for generation of Cherenkov radiation (CR) light capable of activating the at least one photoactivatable drug, and from the CR light, activating inside the subject the at least one photoactivatable drug to thereby treat the disorder.

In one embodiment of the present invention, there is provided a system for treating a subject with a disorder which provides within the subject at least one photoactivatable drug for treatment of the subject, applies initiation energy from at least one source to generate inside the subject a preferential x-ray flux for Cherenkov radiation (CR) light capable of activating the at least one photoactivatable drug, and from the CR light, activating inside the subject the at least one photoactivatable drug to thereby treat the disorder.

It is to be understood that both the foregoing general description of the invention and the following detailed description are exemplary, but are not restrictive of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1A:
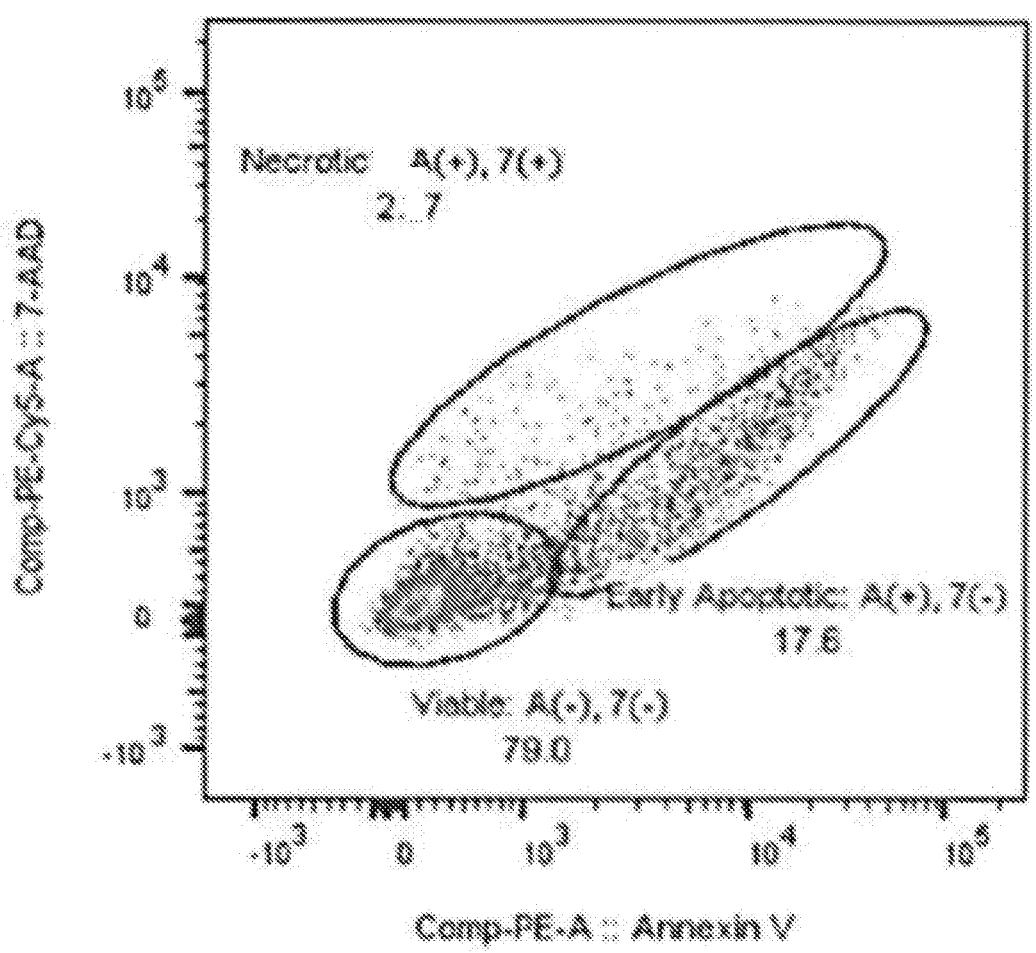
FIGS. 1A and 1B are flow cytometry graphs showing activation of 4T1 cells with 3.3Gy irradiation with and without AMT (psoralen).

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

The prior art approaches described above were limited since the Cherenkov light intensity from a linear accelerator high energy photon or electron beam is an order of magnitude greater than that of PET radionuclides. Hence, other methods than that of PET radionuclides for light activation therapy were needed to optimize current light activation-based therapies.

This invention describes an enhanced therapeutic paradigm for radiotherapy, where the therapeutic treatments are delivered as normal, but an additional highly localized damage component is generated through Cherenkov Light Activation of specific drugs that are activated by UV light. Cherenkov light activation solves the major technical limitation of these drugs (limited depth penetration of UV light) because Cherenkov UV radiation is produced naturally when high energy photons liberate secondary high energy electrons throughout the beam path in tissue. While other groups (Ran et al. 2012) have proposed Cherenkov drug activation using radioactive traces (PET tracers such as FDG), the present invention in one embodiment provides a more effective treatment since the Cherenkov light intensity from a linear accelerator high energy photon or electron beam is an order of magnitude greater than that of PET radionuclides, and can be further optimized through techniques such as x-ray beam filtering (described below).

Drugs that can be activated by Cherenkov light include any UV activated bio-therapeutic, of which psoralen is only one example. Other drugs which are activated by visible radiation may also be indirectly activated by down conversion of the Cherenkov UV light using the energy modulation agents described below. Psoralen is a biologically inert natural compound which transforms to a powerful anti-cancer therapeutic when photo-activated (illuminated with UV light). It has found wide clinical application in treatment sites amenable to UVA light exposure (skin cancer and extracorporeal photopheresis (ECP, FDA approved as UVA-DEX®). Use of more potent forms of psoralen such as AMT can also increase the bio-therapeutic effect.

Figure 1B:
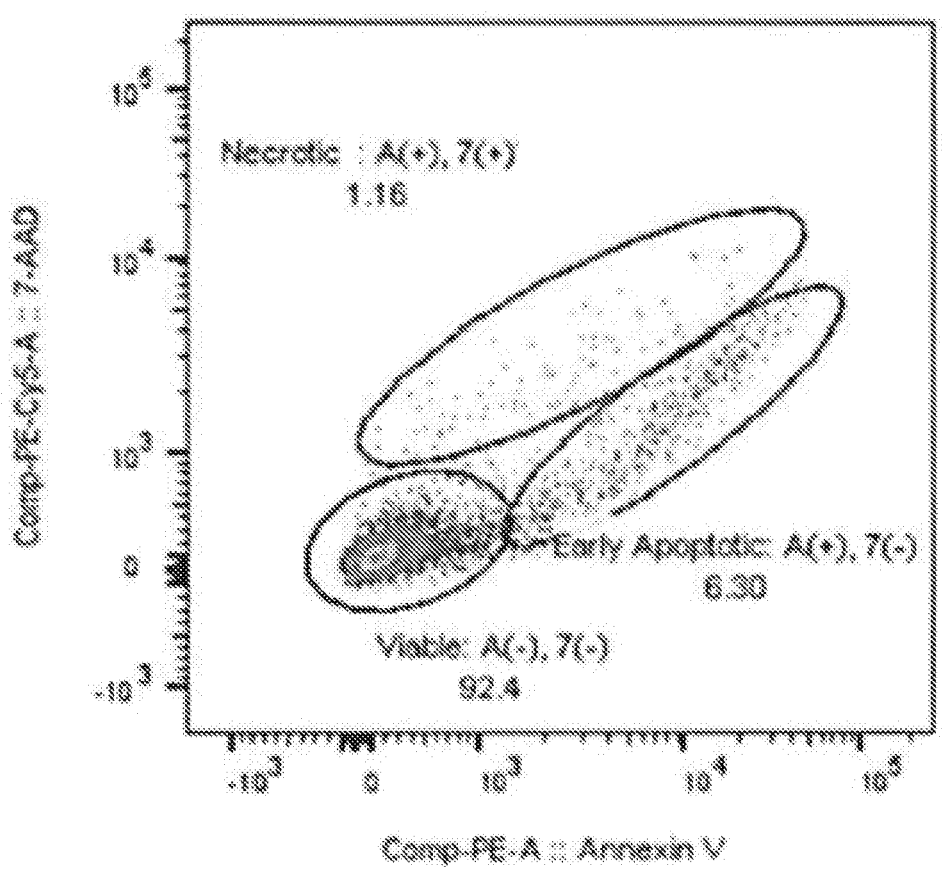

The following experiment shows the effect of psoralen in the form of Aminomethyltrioxsalen (AMT) when activated by Cherenkov light caused by 15 MV photons. Cell exposure to psoralen was minimized for this experiment; the AMT was removed immediately after irradiation. FIGS. 1A and 1B depict flow cytometry for 4T1 cells irradiated with 3.3Gy of 15MV photons with (A) and without (B) psoralen included. Psoralen was removed immediately following irradiation by washing the cells in media. The medium was removed from the well plates, leaving only those cells that are adhered to the plate surface. The increased early apoptotic signal in the A group with psoralen indicates the Cherenekov light activation of psoralen. The results shown are for flow cytometry (Annexin V and 7-AAD) measured at 72 hours after a 3.3Gy irradiation with 15 MV photons; with (A) and without (B) psoralen included. This shows a clear trend towards Annexin V positive when both psoralen and 15MV photons are present, indicating early apoptosis in these cells.

Figure 2A:
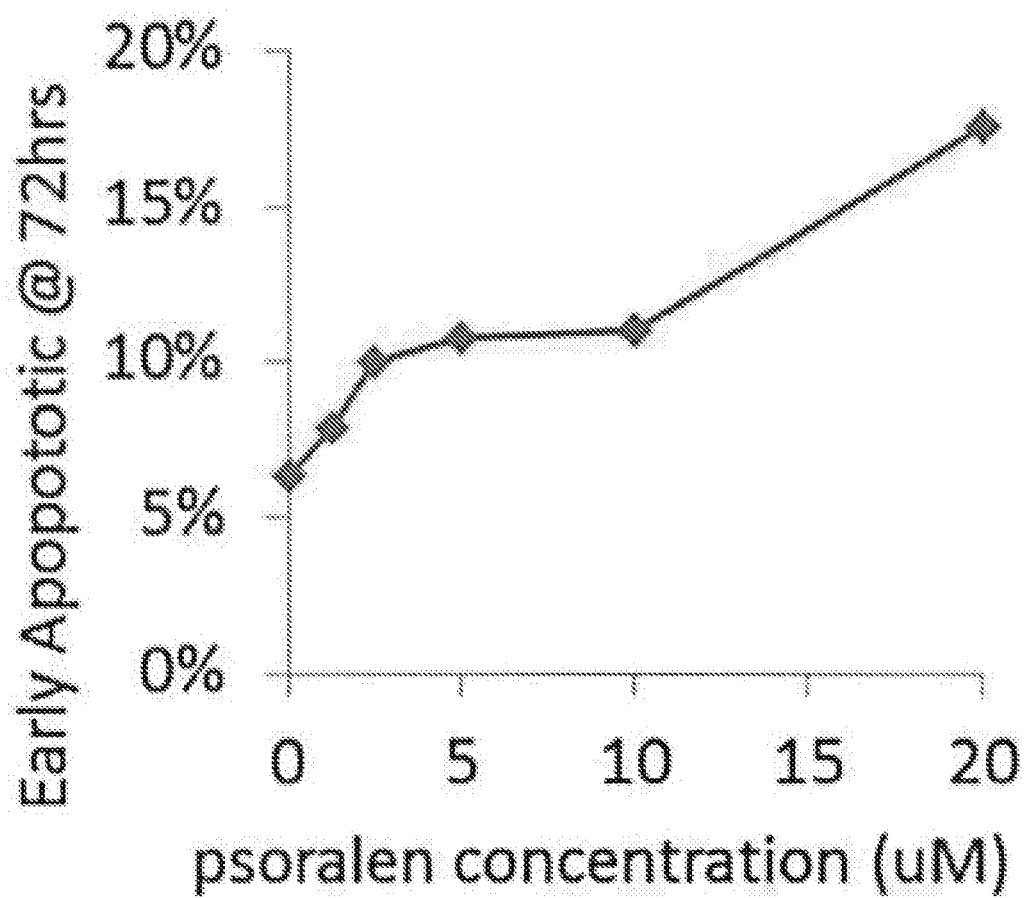
FIG. 2A is a graph showing that AMT (psoralen) exposure was minimized (removed immediately after irradiation).

FIG. 2A depicts early apoptosis in 4T1 cells after irradiation with 3.3Gy or 15 MV photons, as a function of psoralen concentration. The increasing apoptosis as a function of psoralen concentration was not observed for the un-irradiated control, indicating Cherenkov light activation of psoralen.

In various embodiments of the invention, Cherenkov bio-therapeutic photo-activation using a medical linear accelerator (LINAC) is maximized.

One embodiment of the invention optimizes the photon spectrum from the LINAC to achieve maximum useful UV light generation per unit dose (Gy). Spectrum modification is achieved utilizing low-atomic number filters (e.g. carbon) in-place of the conventional flattening filter, which preferentially absorbs low energy photons. Current medical LINACs contain a flattening filter made from aluminum and copper which flatten the beam through beam-hardening to achieve a flat profile at typical treatment depth of 10 cm. The flattening filter is placed in the photon beam path, located after the electron target. It serves to create a flat dose profile over a clinically useable treatment field size (e.g., up to 40 cm×40 cm). Flattening filters are typically cone shaped; they attenuate the center of the field the greatest, so as to achieve the same fluence intensity on the central axis as at the field edge. They are typically composed of dense metals with high atomic weight (such as Tungsten), so as to achieve maximum attenuation in the smallest thickness necessary.

Figure 2B:
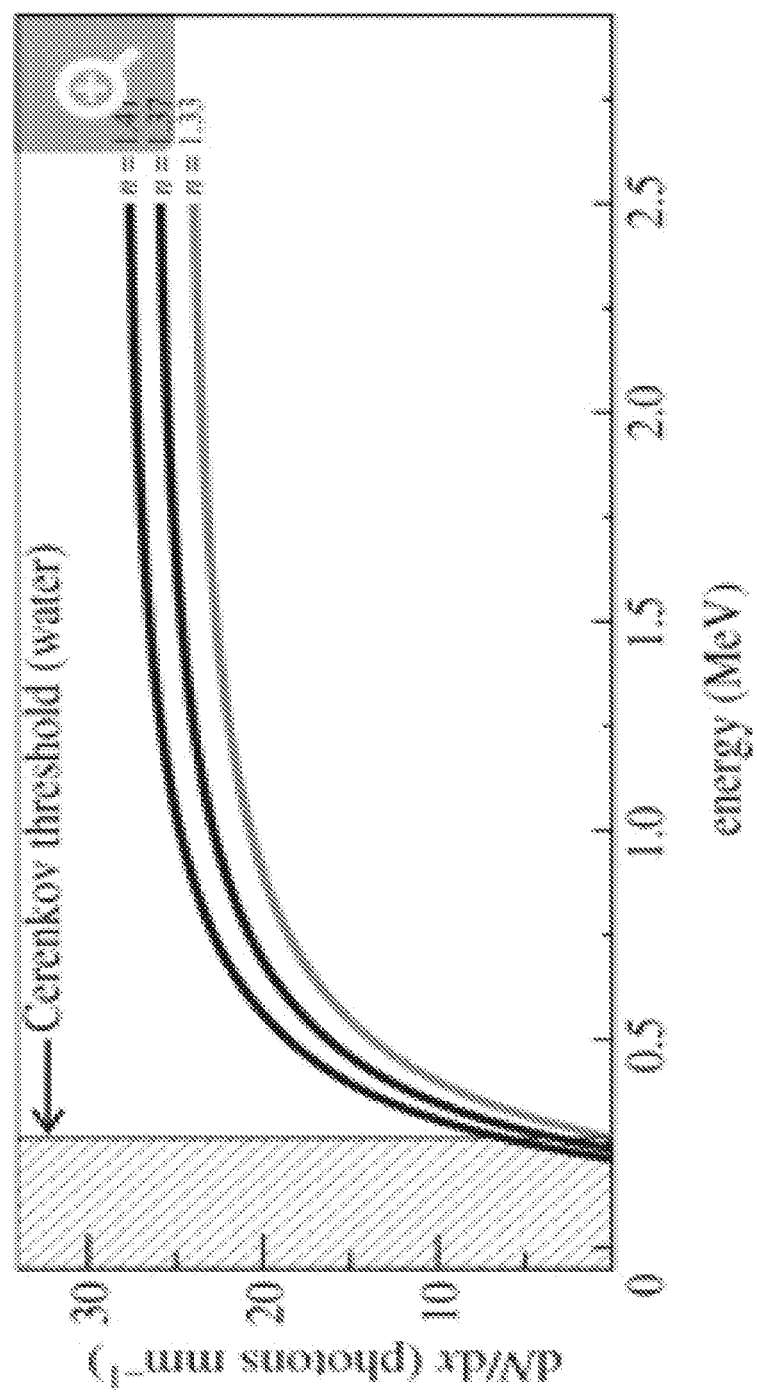
FIG. 2B is a plot showing the number of Cherenkov photons (energy in the wavelength range 400-800 nm) produced per millimeter in water (n=1.33) and materials with other indices of refraction (n=1.37 and 1.41, typical of tissue) as a function of β-particle kinetic.

FIG. 2B is a plot showing the production of Cherenkov radiation in various dielectric media as a function of electron energy. The number of Cherenkov photons produced per millimeter in water (n=1.33) and materials with other indices of refraction (n=1.37 and 1.41, typical of tissue) is shown as a function of ß-particle kinetic energy. Below 0.5 MeV, there is a strong dependence of the light output on the index of refraction. The shaded area shows that particles with energy less than the Cherenkov threshold will not produce any Cherenkov photons. As the particle kinetic energy increases, the Cherenkov intensity asymptotically increases with saturation occurring soon after 1 MeV (from http://rsta.royalsocietypublishing.org/content/369/1955/4605).

In one embodiment of the invention, a preferential x-ray flux in a target medium for inducing a biological change produces more Cherenkov radiation per x-ray dose than its original x-ray spectrum from its original source would have produced upon absorption in the same target medium.

In one embodiment of the invention, a preferential x-ray flux in a target medium for inducing a biological change produces between 5-10% more Cherenkov radiation per x-ray dose than its original x-ray spectrum from its original source would have produced upon absorption in the same target medium.

In one embodiment of the invention, a preferential x-ray flux in a target medium for inducing a biological change produces between 5-20% more Cherenkov radiation per x-ray dose than its original x-ray spectrum from its original source would have produced upon absorption in the same target medium.

In one embodiment of the invention, a preferential x-ray flux in a target medium for inducing a biological change produces between 5-50% more Cherenkov radiation per x-ray dose than its original x-ray spectrum from its original source would have produced upon absorption in the same target medium.

In one embodiment of the invention, a preferential x-ray flux has removed from its original source a higher percentage of lower energy x-rays that do not contribute to Cherenkov radiation (e.g. x-rays of 0.3 MeV or lower) than of higher energy x-rays (e.g. x-rays of 1 MeV or higher) which do contribute to Cherenkov radiation.

In one embodiment of the invention, a preferential x-ray flux has removed from its original source a higher percentage of lower energy x-rays that do not contribute to Cherenkov radiation (e.g. x-rays of 0.5 MeV or lower) than of higher energy x-rays (e.g. x-rays of 1 MeV or higher) which do contribute to Cherenkov radiation.

In one embodiment of the invention, a preferential x-ray flux has removed from its original source a higher percentage of lower energy x-rays that do not contribute to Cherenkov radiation (e.g. x-rays of 1.0 MeV or lower) than of higher energy x-rays (e.g. x-rays of 5 MeV or higher) which do contribute to Cherenkov radiation.

In one embodiment of the invention, a preferential x-ray flux has removed from its original source a higher percentage of lower energy x-rays that do not contribute to Cherenkov radiation (e.g. x-rays of 1.0 MeV or lower) than of higher energy x-rays (e.g. x-rays of 10 MeV or higher) which do contribute to Cherenkov radiation.

In this embodiment of the invention, the low-atomic number filter would have a completely different purpose from the conventional flattening filter. More specifically, the purpose of the low-atomic number filter would be to alter the x-ray fluence spectrum of the LINAC beam in order to maximize Cherenkov light production in the tumor per unit dose of radiation. In essence, the low-atomic number filter of the invention would have a thickness and mass composition that would remove the lower energy x-ray photons that result in only a small amount of or no Cherenkov radiation from the beam while transmitting the higher energy x-ray photons. Low-atomic number filters (such for example filters made with a substantial fraction of carbon) would exhibit this kind of x-ray photon transmittance useful in the present invention. While not limited to the following thicknesses, depending on the materials selected, the thickness of the low mass filter preferentially absorbing lower energy x-rays can range from mm to cm or more in thickness.

In one embodiment of the invention, a preferential x-ray flux in a target medium for inducing a biological change produces more Cherenkov radiation per x-ray dose than its original x-ray spectrum filtered by a flattening filter would have produced upon absorption in the same target medium.

In one example of a low mass filter, the filter comprises a carbon filter (e.g., a graphite or amorphous carbon filter) having a thickness in the range of 0.5 to 50 cm, or 1 to 20 cm, or 2 to 10 cm, or 5 to 7 cm, or ranges in between and overlapping. The x-ray photons transit the thickness of the carbon filter where the lower energy x-ray photons are preferentially absorbed.

In another example of a low mass filter, the filter comprises a natural or synthetic polymer filter (e.g., a polyurethane filter or polytetrafluorethylene filter or a silicone filter) having a thickness in the range of 0.5 to 50 cm, or 1 to 20 cm, or 2 to 10 cm, or 5 to 7 cm, or ranges in between and overlapping. The x-ray photons transit the thickness of the polymer filter where the lower energy x-ray photons are preferentially absorbed.

In one embodiment of the invention, the invention utilizes "flattening filter free" radiotherapy beams, for which the flattening filter is eliminated. These beams have the advantage of increased dose rate and the passing of higher energy x-rays which would produce a higher percentage of Cherenkov radiation, but at the cost of the beam being un-flattened. However, this disadvantage can be offset using multi-leaf collimators which are common on modern linear accelerators.

Another embodiment of the invention involves combining the bio-therapeutic Cherenkov radiation with fluorophores which capture the Cherenkov light emitted at wavelengths outside the range for drug activation, and re-emit at energies within the activation range. In this embodiment, fluorophores capture portions of the Cherenkov spectrum and re-emit in the ultraviolet and the visible range which is useful for psoralen (or equivalent) activation. In one embodiment, fluorophores that can absorb in the UV-blue range and emit at a lower energy (e.g., toward red) would be suitable for activating drugs that are sensitive to the visible light (i.e., for drugs which have peak absorption in the visible).

In one embodiment, organic molecules can be used that down-convert from X-Ray into UV and Visible. Organic compounds can be used to achieve the same down conversion. Anthracene and anthracene based compounds can be used. Anthracene exhibits a blue (400-500 nm peak) fluorescence under ultraviolet light. Antharacene also exhibits fluorescence under X-Ray energy.

Accordingly, in one embodiment of the invention, both x-rays in the target medium and Cherenkov radiation in the target medium can be down-converted to light matched to the photoactive drug or determined to be capable of activating the photoactive drug.

Various plastic scintillators, plastic scintillator fibers and related materials are made of polyvinyltoluene or styrene and fluors can be used. These and other formulations are commercially available, such as from Saint Gobain Crystals, as BC-414, BC-420, BC-422, or BCF-10.

| Phosphor | Product Reference | Peak Emission (nm) |
| --- | --- | --- |
| Organic | BC-414 | 392 |
| Organic | BC-420 | 391 |
| Organic | BC-422 | 370 |

Other polymers are able to emit in the visible range and these include:

| Phosphor (Fiber Forms) | Product Reference | Peak Emission (nm) | # of Photons Per MeV |
| --- | --- | --- | --- |
| Organic | BCF-10 | 432 | 8000 |
| Organic | BC-420 | 435 | 8000 |
| Organic | BC-422 | 492 | 8000 |

These organic molecules could then be used to assist in activation of a drug such as psoralen because these organic molecules would be able to capture a part of the CR spectrum and a part of the x-rays escaping without use and provide an additional source of internal UV light generated inside the patient or subject.

Another embodiment involves selection of the linear accelerator dose rate to optimize the drug activation by the Cherenkov light. The following examples are added by way of illustration and not limitation.

EXAMPLES

1. Enhancing SRS/SBRT Treatment Through Cherenkov Light Activation of Psoralen (CLAP)

The following are appropriate design criteria for optimizing the treatment effect:
   a) Maximize the Cherenkov light output (per Gy) from a Varian linear accelerator by optimizing the photon spectrum using the above-noted low-mass filters. In particular, a filter made of low-Z material (e.g. carbon as discussed above) is used in this embodiment to maximize Cherenkov output in tissue. The filter replaces the standard flattening filter for 15+MV photon beams or could be used in addition to the standard flattening filter.
   b) Optimize the efficacy of Cherenkov Light Activation of Psoralen (CLAP) in-vitro in malignant cell lines relevant to liver Stereotactic Body Radiation Therapy (SBRT) and stereotactic radiosurgery (SRS). Cherenkov light emission in tissue is a normal phenomenon accompanying SBRT/SRS, which is normally ignored. In SRS, the doses are typically higher which could be important because Cherenkov production is proportional to dose. In SRS, one typically delivers 20 Gy in a single fraction. In one embodiment, the Cherenkov light photo-activates powerful anti-cancer bio-therapeutics (e.g., psoralen) with potential to add a long-term immunogenic response to SBRT/SRS treatment. The above-noted fluorophores or down converting energy modulation agents in this embodiment maybe used to capture the Cherenkov light emitted at wavelengths outside the range for drug activation, and re-emit at energies within the activation range.

In the enhanced therapeutic paradigm for SBRT and SRS of the invention, the SBRT and SRS treatments are delivered as normal, but an additional highly localized "damage" component (due to photoactivation of psoralen for example) is generated through Cherenkov Light Activation of Psoralen (CLAP). As noted in the background, psoralen is a biologically inert natural compound which transforms to a powerful anti-cancer therapeutic when photo-activated (illuminated with LT light). In addition to the reaction pathways described in the background to activate psoralen, in one embodiment of the invention, under exposure to the Cherenkov radiation, psoralen can be made to form monoadducts or photoadducts 4',5' or photoadducts 3,4 or crosslink (where both types of photoadducts.

Psoralen and its derivatives have found wide clinical application in treatment sites amenable to UVA light exposure (skin cancer and extracorporeal photopheresis (ECP, FDA approved as UVADEX®). Psoralen therapy has been used mostly for limited superficial or ECP applications because of the technical difficulty in generating UVA light deep within tissue. Meanwhile, the CLAP enhanced therapeutic treatment of the present invention addresses this limitation by using Cherenkov UV and blue radiation produced when high energy photons liberate secondary high energy electrons throughout the beam path in tissue. In one embodiment of the invention, the Cherenkov light from radiotherapy can permit real-time surface dose measurements, thereby monitoring of the total Gy exposure. For example, the Cherenkov light reflected off the surface of the patient can be imaged using a UV sensitive camera. The Cherenkov light is proportional to the radiation dose delivered. Workers have described in Medical Physics 38 (7) pages 4127-4132 (2011), the entire contents of which are incorporated herein by reference, this approach for determining a dose.

In one embodiment of the invention, SBRT/SRS treatments are delivered with an optimized LINAC photon spectrum (using for example the low-mass filter described above) and generate sufficient psoralen photo-activation which, in turn, produces a long-term immunogenic component induced by the patient's autoimmune response to the "damaged" cells.

In one aspect of the invention, a system (and corresponding method) is provided for imaging or treating a tumor in a human or animal body. The system includes a pharmaceutical carrier including a photoactivatable drug and an optional pharmaceutical carrier, an x-ray or high energy electron or proton source capable of producing energies for the x-rays, electrons, or protons which yield in a target material CR light, and a processor programmed to control a dose of x-rays or electrons to the tumor for production of CR light inside or in the vicinity of the tumor to activate the photoactivatable drug.

The method in one embodiment of the invention includes injecting into a vicinity of and inside the tumor a pharmaceutical carrier including the photoactivatable drug, applying x-ray or high energy electrons or protons to the tumor, and producing the CR light inside or in the vicinity of the tumor to activate the photoactivatable drug. In one embodiment of the invention, the low mass filter predominantly transmits x-ray photons having energies predominantly greater than 0.5 MeV, or greater than 1.0 MeV, or greater than 1.5 MeV, or greater than 2.0 MeV. While described with respect to CR activation, the present invention can also use energy modulation agents (e.g., phosphors or other down conversion media), combinations of different down conversion media, upconversion media, combinations of different up conversion media, and/or combinations of different up and down conversion media. These different media are detailed below in the various embodiments.

Radiation from the energy modulation agents can assist or supplement the CR radiation to alter the biological activity of the medium, as described in more detail below.

Accordingly, as noted above, in one embodiment of this invention, there is provided a system or method for light stimulation within a medium. The system has a high energy x-ray or electron or proton source which provides high energy x-rays or electrons or protons into the medium to be treated to produce CR light inside the medium to be treated, especially a biological medium.

In certain embodiments of the invention, it is preferred to target the tissue such that radiation dose can be maximized in the target area, while being minimized in skin and superficial dose. Such targeting can be preferably done with appropriate collimation, using as an associated imaging system, a fan beam or cone beam x-ray system, or combinations thereof. Other targeting mechanisms include axial and angular mA modulation of a Computed Tomograph (CT) system, and spectrum shaping through k-edge or crystalline filtering to "tune" the x-ray energy precisely to where the medium to be treated shows optimum CR light production or energy-converting or energy modulation agent in the medium shows maximum sensitivity.

In one embodiment, the initiation energy is capable of penetrating completely through the medium. Within the context of the invention, the phrase "capable of penetrating completely through the medium" is used to refer to energy capable of penetrating a container to any distance necessary to activate the activatable agent within the medium. It is not required that the energy applied actually pass completely through the medium, merely that it be capable of doing so in order to permit penetration to any desired distance to internally generate CR light in a vicinity of the activatable agent, such as by targeting the focus of the x-ray beam and thus the desired x-ray dose in the desired tissue. The type of energy source chosen will depend on the medium itself.

Regardless of method of treatment, psoralen and psoralen derivatives are of interest for many of the biological applications of this invention.

Photoactivation Treatments of the Invention:

For the treatment of cell proliferation disorders, an initiation energy source can provide an energy that generates CR light to activate an activatable pharmaceutical agent to treat target cells within a subject. In one embodiment, the initiation energy is applied indirectly to the activatable pharmaceutical agent, preferably in proximity to the target cells.

Within the context of here, the phrase "applied indirectly" (or variants of this phrase, such as "applying indirectly", "indirectly applies", "indirectly applied", "indirectly applying", etc.), when referring to the application of the initiation energy, means the penetration by the initiation energy into the subject beneath the surface of the subject and to the activatable pharmaceutical agent within a subject.

Although not intending to be bound by any particular theory or be otherwise limited in any way, the following theoretical discussion of scientific principles and definitions are provided to help the reader gain an understanding and appreciation of the invention.

As used herein, the term "subject" is not intended to be limited to humans, but may also include animals, plants, or any suitable biological organism.

As used herein, the phrase "cell proliferation disorder" refers to any condition where the growth rate of a population of cells is less than or greater than a desired rate under a given physiological state and conditions. Although, preferably, the proliferation rate that would be of interest for treatment purposes is faster than a desired rate, slower than desired rate conditions may also be treated by methods of the invention. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Particularly preferred cell proliferation disorders for treatment using the present methods are cancer, *staphylococcus aureus* (particularly antibiotic resistant strains such as methicillin resistant *staphylococcus aureus* or MRSA), and autoimmune disorders.

As used herein, an "activatable agent" is an agent that normally exists in an inactive state in the absence of an activation signal (e.g., one or more photons). When the agent is activated by an activation signal under activating conditions, the agent is capable of producing a desired pharmacological, cellular, chemical, electrical, or mechanical effect in a medium (i.e. a predetermined change in the medium).

Signals that may be used to activate a corresponding agent may include, but are not limited to, photons of specific wavelengths (e.g. x-rays, ultraviolet, or visible light). For example, an activatable agent, such as a photosensitizer, may be activated by UV-A radiation (e.g., by UV-A radiation generated internally in the medium). For example, an activatable agent, such as a photosensitizer, may be activated by UV—B or UV-C radiation. Once activated, the agent in its active-state may then directly proceed to produce a predetermined change.

When activated, the activatable agent may effect changes that include, but are not limited to an increase in organism activity, a decrease in organism activity, apoptosis, and/or a redirection of metabolic pathways.

As used herein, an "activatable pharmaceutical agent" (alternatively called a "photoactive agent" or PA) is an agent that normally exists in an inactive state in the absence of an activation signal. When the agent is activated, it is capable of affecting the desired pharmacological effect on a target cell (i.e. preferably a predetermined cellular change).

A photoactive compound that achieves its pharmaceutical effect by binding (with mono adducts formation or cross links formation) to certain cellular structure in its active state may require physical proximity to the target cellular structure when the activation signal is delivered. Some examples of activating conditions may include, but are not limited to, temperature, pH, location, state of the cell, presence or absence of co-factors. Selection of an activatable pharmaceutical agent greatly depends on a number of factors such as the desired cellular change, the desired form of activation, as well as the physical and biochemical constraints that may apply.

When activated for example by CR light, the activatable pharmaceutical agent may affect cellular changes that include, but are not limited to, apoptosis, redirection of metabolic pathways, up-regulation of certain genes, down-regulation of certain genes, secretion of cytokines, alteration of cytokine receptor responses, production or modulation of reactive oxygen species or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include modulation of or releasing metabolites upon activation to interfere with normal metabolic pathways, releasing chemical signals (e.g. agonists or antagonists) upon activation to alter the targeted cellular response, and other suitable biochemical or metabolic alterations.

In one preferred embodiment, the activatable pharmaceutical agent is capable of chemically binding to the DNA or mitochondriat at a therapeutically effective amount. In this embodiment, the activatable pharmaceutical agent, preferably a photoactivatable agent, is exposed in situ to light internally generated for example by CR and/or an energy modulation agent.

An activatable agent may be a small molecule; a biological molecule such as a protein, a nucleic acid or lipid; a supramolecular assembly; a nanoparticle; a nanostructure, or combinations thereof; or any other molecular entity having a pharmaceutical activity once activated.

The activatable agent may be derived from a natural or synthetic origin. Any such molecular entity that may be activated by a suitable activation signal source to effect a predetermined cellular change may be advantageously employed in the invention.

Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD], alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Additional photoactive agents include, but are not limited to, carbene precursors, nitrene precursors, thio derivatives, benzophenones, and halogenated pyrimidines. Such photochemistries are routinely employed to achieve protein-DNA photocross-links but none has been achieved using an indirect method as presented herein, for example where X-Ray radiation is converted to UV radiation to activate the species and achieve DNA photocross-links.

Endogenously-based derivatives include synthetically derived analogs and homologs of endogenous photoactivated molecules, which may have or lack lower (1 to 5 carbons) alkyl or halogen substituents of the photosensitizers from which they are derived, and which preserve the function and substantial non-toxicity. Endogenous molecules are inherently non-toxic and may not yield toxic photoproducts after photoradiation.

The nature of the predetermined cellular change will depend on the desired pharmaceutical outcome. Exemplary cellular changes may include, but are not limited to, morphologic changes, apoptosis, necrosis, up-regulation of certain genes, down-regulation of certain genes, modulation of or secretion of cytokines, alteration of cytokine receptor responses, or a combination thereof.

When activated for example by CR light, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, production of reactive oxygen species or combinations thereof.

A preferred method of treating a cell proliferation disorder of the invention administers a photoactivatable agent to a patient, stimulates the photoactivatable agent by CR light to induce cell damage (or kill), and generates an auto vaccine effect.

Additionally, energy modulation agents may be included in the medium to be treated. The energy modulation agents could be used to supplement the internally generated CR by downconverion of x-rays into ultraviolet or visible light. The energy modulation agents could be used to down-convert a portion of the CR spectrum or up-convert a portion of the CR spectrum.

As used here, an "energy modulation agent" refers to an agent that is capable of receiving an energy input from a source and then re-emitting a different energy to a receiving target. Energy transfer among molecules may occur in a number of ways. The form of energy may be electronic, thermal, electromagnetic, kinetic, or chemical in nature. Energy may be transferred from one molecule to another (intermolecular transfer) or from one part of a molecule to another part of the same molecule (intramolecular transfer). For example, a modulation agent may receive electromagnetic energy and re-emit the energy in the form of thermal energy which otherwise contributes to heating the environment in vicinity of the light emission. In various embodiments, the energy modulation agents receive higher energy (e.g. x-ray) and re-emits in lower energy (e.g. UV-A). Some modulation agents may have a very short energy retention time (on the order of fs, e.g. fluorescent molecules) whereas others may have a very long half-life (on the order of minutes to hours, e.g. luminescent or phosphorescent molecules). The energy modulation agent materials can preferably include any materials that can absorb X ray and emit light in order to excite the PA molecule.

Quantum dots, semiconductor nanostructures and various materials related to quantum dots, semiconductor materials, etc. can be used as energy modulation agents. Scintillator materials can be used as energy modulation agents. Various scintillator materials can be used as energy modulation agents since they absorb X-ray and emit luminescence emission, which can be used to excite the PA system. For example, single crystals of molybdates can be excited by X-ray and emit luminescence around 400 nm [Mirkhin et al, *Nuclear Instrum. Meth. In Physics Res. A,* 486, 295 (2002, the entire contents of which are incorporated herein by reference]. For example CdS (or CsCl) exhibit luminescence when excited by soft X-ray [Jaegle et al, *J. Appl. Phys.,* 81, 2406, 1997, the entire contents of which are incorporated herein by reference]. XEOL materials such as lanthanides or rare earth materials can be used as energy modulation agents.

Suitable energy modulation agents include, but are not limited to, a phosphor, a scintillator, a biocompatible fluorescing metal nanoparticle, fluorescing dye molecule, gold nanoparticle, quantum dots, such as a water soluble quantum dot encapsulated by polyamidoamine dendrimers, a luciferase, a biocompatible phosphorescent molecule, a combined electromagnetic energy harvester molecule, an up-converter, a lanthanide chelate capable of intense luminescence, metals (gold, silver, etc); semiconductor materials; materials that exhibit X-ray excited luminescence (XEOL); organic solids, metal complexes, inorganic solids, crystals, rare earth materials (lanthanides), polymers, and materials that exhibit excitonic properties.

In a preferred embodiment, the energy modulation agents include down converters (such as for example phosphors which can convert x-ray or other high energy photon or particle into visible light. These down converters when used in combination can activate a variety of UV-stimulated photoreactions as well as activate any visible light activated reactions.

Examples of luminescing particles (down converters) can include gold particles (such as for example the nanoparticles of gold), BaFBr:Eu particles, CdSe particles, $Y_2O_3$:$Eu^{3+}$ particles, and/or other known stimulated luminescent materials such as for example ZnS: $Mn^{2+}$; ZnS:$Mn^{2+}$,$Yb^{3+}$, $Y_2O_3$: $Eu^{3+}$; BaFBr:$Tb^{3+}$; and $YF_3$:$Tb^{3+}$. More specific examples of the downconverters include, but are not limited to: BaFCl:$Eu^{2+}$, $BaSO_4^-$:$Eu^{2+}$, LaOBr:$Tm^{3+}$ $YTaO_4$, YTaO$_4$:Nb, CaWO$_4$, LaOBr:Tb$^{3+}$, Y$_2$O$_2$S:Tb$^{3+}$, ZnS:Ag, (Zn,Cd)S:Ag, Gd$_2$O$_2$S:Tb$^{3+}$, La$_2$O$_2$S:Tb$^{3+}$.

In one aspect of the invention, a downconverting energy modulation agent can comprise inorganic particulates selected from the group consisting of: metal oxides; metal sulfides; doped metal oxides; and mixed metal chalcogenides. In one aspect of the invention, the downconverting material can comprise at least one of Y$_2$O$_3$, Y$_2$O$_2$S, NaYF$_4$, NaYbF$_4$, YAG, YAP, Nd$_2$O$_3$, LaF$_3$, LaCl$_3$, La$_2$O$_3$, TiO$_2$, LuPO$_4$, YVO$_4$, YbF$_3$, YF$_3$, Na-doped YbF$_3$, ZnS; ZnSe; MgS; CaS; CaWO$_4$, CaSiO$_2$:Pb, and alkali lead silicate including compositions of SiO$_2$, B$_2$O$_3$, Na$_2$O, K$_2$O, PbO, MgO, or Ag, and combinations or alloys or layers thereof. In one aspect of the invention, the downconverting material can include a dopant including at least one of Er, Eu, Yb, Tm, Nd, Mn Tb, Ce, Y, U, Pr, La, Gd and other rare-earth species or a combination thereof. The dopant can be included at a concentration of 0.01%-50% by mol concentration.

In one aspect of the invention, the downconverting energy modulation agent can comprise materials such as ZnSeS:Cu, Ag, Ce, Tb; CaS: Ce,Sm; La$_2$O$_2$S:Tb; Y$_2$O$_2$S:Tb; Gd$_2$O$_2$S: Pr, Ce, F; LaPO$_4$. In other aspects of the invention, the downconverting material can comprise phosphors such as ZnS:Ag and ZnS:Cu, Pb. In other aspects of the invention, the downconverting material can be alloys of the ZnSeS family doped with other metals. For example, suitable materials include ZnSe$_x$S$_y$:Cu, Ag, Ce, Tb, where the following x, y values and intermediate values are acceptable: x:y; respectively 0:1; 0.1:0.9; 0.2:0.8; 0.3:0.7; 0.4:0.6; 0.5: 0.5; 0.6:0.4; 0.7:0.3; 0.8:0.2; 0.9:0.1; and 1.0:0.0.

In other aspects of the invention, the downconverting energy modulation agent can be materials such as sodium yttrium fluoride (NaYF$_4$), lanthanum fluoride (LaF$_3$), lanthanum oxysulfide (La$_2$O$_2$S), yttrium oxysulfide (Y$_2$O$_2$S), yttrium fluoride (YF$_3$), yttrium gallate, yttrium aluminum garnet (YAG), gadolinium fluoride (GdF$_3$), barium yttrium fluoride (BaYFs, BaY$_2$F$_8$), gadolinium oxysulfide (Gd$_2$O$_2$S), calcium tungstate (CaWO$_4$), yttrium oxide:terbium (Yt$_2$O$_3$Tb), gadolinium oxysulphide:europium (Gd$_2$O$_2$S:Eu), lanthanum oxysulphide:europium (La$_2$O$_2$S: Eu), and gadolinium oxysulphide:promethium, cerium, fluorine (Gd$_2$O$_2$S:Pr,Ce,F), YPO$_4$:Nd, LaPO$_4$:Pr, (Ca,Mg)SO$_4$: Pb, YBO$_3$:Pr, Y$_2$SiO$_5$:Pr, Y$_2$Si$_2$O$_7$:Pr, SrLi$_2$SiO$_4$:Pr,Na, and CaLi$_2$SiO$_4$:Pr.

In other aspects of the invention, the downconverting energy modulation agent can be near-infrared (NIR) down-conversion (DC) phosphors such as KSrPO$_4$:Eu$^{2+}$, Pr$^{3+}$, or NaGdF$_4$:Eu or Zn$_2$SiO$_4$:Tb$^{3+}$,Yb$^{3+}$ or P3-NaGdF$_4$ co-doped with Ce$^{3+}$ and Tb$^{3+}$ ions or Gd$_2$O$_2$S:Tm or BaYFs:Eu$^{3+}$ or other down converters which emit NIR from visible or UV light exposure (as in a cascade from x-ray to UV to NIR) or which emit NIR directly after x-ray or e-beam exposure.

In one embodiment of the invention, some of the phosphors noted above can absorb in the 390 to 410 nm range and then in turn down convert the CR radiation into red shifted emissions for activation in the visible. As an example, the excitation wavelength can be between 300 nm and 450 nm, and the emission can be centered around 650 nm as is the case for 6MgO. As$_2$O$_5$:Mn$^{4+}$ and for 3.5MgO 0.5MgF$_2$GeO$_2$:Mn$^{2+}$.

In one aspect of the invention, an up-converting energy modulation agent can be used which is activated by for example an infrared or near infrared source such as a laser. The up-converting energy modulation agent can be at least one of Y$_2$O$_3$, Y$_2$O$_2$S, NaYF$_4$, NaYbF$_4$, YAG, YAP, Nd$_2$O$_3$, LaF$_3$, LaCl$_3$, La$_2$O$_3$, TiO$_2$, LuPO$_4$, YVO$_4$, YbF$_3$, YF$_3$, Na-doped YbF$_3$, or SiO$_2$ or alloys or layers thereof.

Furthermore, the luminescing particles (down converters, mixtures of down converters, up converters, mixtures of up converters, and combinations thereof) of the invention described here can be coated with insulator materials such as for example silica which will reduce the likelihood of any chemical interaction between the luminescing particles and the medium. For biological applications of inorganic nanoparticles, one of the major limiting factors is their toxicity.

Generally speaking, all semiconductor nanoparticles are more or less toxic. For biomedical applications, nanoparticles with toxicity as low as possible are desirable or else the nanoparticles have to remain separated from the medium. Pure TiO$_2$, ZnO, and Fe$_2$O$_3$ are biocompatible. CdTe and CdSe are toxic, while ZnS, CaS, BaS, SrS and Y$_2$O$_3$ are less toxic. In addition, the toxicity of nanoparticles can result from their inorganic stabilizers, such as TGA, or from dopants such as Eu$^{2+}$, Cr$^{3+}$ or Nd$^{3+}$. Other suitable energy modulation agents which would seem the most biocompatible are zinc sulfide, ZnS:Mn$^{2+}$, ferric oxide, titanium oxide, zinc oxide, zinc oxide containing small amounts of Al$_2$O$_3$ and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; Er$^{3+}$ doped BaTiO$_3$ nanoparticles, Yb$^{3+}$ doped CsMnCl$_3$ and RbMnCl$_3$, BaFBr:Eu$^{2+}$ nanoparticles, cesium iodide, bismuth germanate, cadmium tungstate, and CsBr doped with divalent Eu.

In various embodiments of the invention, the following luminescent polymers are also suitable as energy modulation agents: poly(phenylene ethynylene), poly(phenylene vinylene), poly(p-phenylene), poly(thiophene), poly(pyridyl vinylene), poly(pyrrole), poly(acetylene), poly(vinyl carbazole), poly(fluorenes), and the like, as well as copolymers and/or derivatives thereof.

While many of the energy modulation agents of the invention are down conversion agents (i.e. where higher energy excitation produces lower energy emission), U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 including the ZnS as well as Er$^{3+}$ doped BaTiO$_3$ nanoparticles and Yb$^{3+}$ doped CsMnCl$_3$ are suitable in various embodiments of the invention.

Further, in various embodiments of the invention, the up converters can be used in combination with the down converters (or mixtures of down converters) or in combination with various up converters. Various up converters suitable for this invention include CdTe, CdSe, ZnO, CdS, Y$_2$O$_3$, MgS, CaS, SrS and BaS. Such up conversion materials may be any semiconductor and more specifically, but not by way of limitation, sulfide, telluride, selenide, and oxide semiconductors and their nanoparticles, such as Zn$_{1-x}$Mn$_x$S$_y$, Zn$_{1-x}$Mn$_x$Se$_y$, Zn$_{1-x}$Mn$_x$Te$_y$, Cd$_{1-x}$MnS$_y$, Cd$_{1-x}$Mn$_x$Se$_y$, Cd$_{1-x}$Mn$_x$Te$_y$, Pb$_{1-x}$Mn$_x$S$_y$, Pb$_{1-x}$Mn$_x$Se$_y$, Pb$_{1-x}$Mn$_x$Te$_y$, Mg$_{1-x}$MnS$_y$, Ca$_{1-x}$Mn$_x$S$_y$, Ba$_{1-x}$Mn$_x$S$_y$ and Sr$_{1-x}$, etc. (wherein, 0<x≤1, and 0<y≤1). Complex compounds of the above-described semiconductors are also contemplated for use in the invention—e.g. (M$_{1-z}$N$_z$)$_{1-x}$Mn$_x$A$_{1-y}$B$_y$ (M=Zn, Cd, Pb, Ca, Ba, Sr, Mg; N=Zn, Cd, Pb, Ca, Ba, Sr, Mg; A=S, Se, Te, O; B=S, Se, Te, O; 0<x≤1, 0<y≤1, 0<z≤1). Two examples of such complex compounds are Zn$_{0.4}$Cd$_{0.4}$Mn$_{0.2}$S and Zn$_{0.9}$Mn$_{0.1}$S$_{0.8}$Se$_{0.2}$. Additional conversion materials include insulating and nonconducting materials such as $BaF_2$, $BaFBr$, and $BaTiO_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn,Yb; MgS; Mn, Yb; CaS; Mn,Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, ... $0<z\leq1$, $o<q\leq1$).

Indeed, some nanoparticles such as $ZnS:Tb^{3+}$, $Er^{3+}$; $ZnS:Tb^{3+}$; $Y_2O_3:Tb^{3+}$; $Y_2O_3:Tb^{3+}$, $Er^{3+}$; $ZnS:Mn^{2+}$; $ZnS:Mn$, $Er^{3+}$ are known in the art to have two functions, capable of functioning for both down-conversion luminescence and upconversion luminescence.

To reduce the toxicity or to make these nanoparticles bio-inert or biocompatible, one embodiment of the invention described here coats these nanoparticles with silica. Silica is used as a coating material in a wide range of industrial colloid products from paints and magnetic fluids to high-quality paper coatings. Further, silica is both chemically and biologically inert and also is optically transparent. Other coatings suitable for this invention include a polymethyl methacrylate (PMMA) coating and an ethyl-cellulose coating.

Additionally, the energy modulation agent can be used alone or as a series of two or more energy modulation agents wherein the energy modulation agents provide an energy cascade from the light of the phosphors or scintillators. Thus, the first energy modulation agent in the cascade will absorb the CR, convert it to a different energy which is then absorbed by the second energy modulation in the cascade, and so forth until the end of the cascade is reached with the final energy modulation agent in the cascade emitting the energy necessary to activate the activatable pharmaceutical agent.

In one embodiment of the invention, a chemical reaction cascade can be triggered. The CR can activate a chemical which in turn can activate a bio-therapeutic in parallel to or independent of a photonic pathway.

The energy modulation agents or the photoactivatable agent may further be coupled to a carrier for cellular targeting purposes. For example, a UV-A emitting energy modulation agent may be concentrated in the tumor site by physical insertion or by conjugating the UV-A emitting energy modulation agent with a tumor specific carrier, such as an antibody, nucleic acid, peptide, a lipid, chitin or chitin-derivative, a chelate, a surface cell receptor, molecular imprints, aptamers, or other functionalized carrier that is capable of concentrating the UV-A emitting source in a specific target tumor.

A method in accordance with one embodiment of the invention utilizes the principle of energy transfer to and among molecular agents to control delivery and activation of cellular changes by irradiation such that delivery of the desired effect is more intensified, precise, and effective than the conventional techniques. At least one energy modulation agent can be administered to the subject which adsorbs, intensifies or modifies the CR into an energy that effects a predetermined cellular change in the target structure. The energy modulation agent may be located around, on, or in the target structure. Further, the energy modulation agent can transform CR into a photonic energy that effects a predetermined change in the target structure. In one embodiment, the energy modulation agent decreases the wavelength of the CR (down convert). In another embodiment, the energy modulation agent can increase the wavelength of the CR (up convert). In a different embodiment, the energy modulation agent is one or more members selected from a biocompatible fluorescing metal nanoparticle, fluorescing metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a biocompatible phosphorescent molecule, a combined electromagnetic energy harvester molecule, and a lanthanide chelate exhibiting intense luminescence.

In general, photoactivatable agents may be stimulated by light from CR and/or light from the energy modulation agents, leading to subsequent irradiation, resonance energy transfer, exciton migration, electron injection, or chemical reaction, to an activated energy state that is capable of effecting the predetermined cellular change desired. In a one embodiment, the photoactivatable agent, upon activation, binds to DNA or RNA or other structures in a cell. The activated energy state of the agent is capable of causing damage to cells, inducing apoptosis. The mechanism of apoptosis is associated with an enhanced immune response that reduces the growth rate of cell proliferation disorders and may shrink solid tumors, depending on the state of the patient's immune system, concentration of the agent in the tumor, sensitivity of the agent to stimulation, and length of stimulation.

When drug molecules absorb excitation light, electrons undergo transitions from the ground state to an excited electronic state. The electronic excitation energy subsequently relaxes via radiative emission (luminescence) and radiationless decay channels. When a molecule absorbs excitation energy, it is elevated from $S_o$ to some vibrational level of one of the excited singlet states, $S_n$, in the manifold $S_1, \ldots, S_n$. In condensed media (tissue), the molecules in the S, state deactivate rapidly, within $10^{-13}$ to $10^{-11}$ s via vibrational relaxation (VR) processes, ensuring that they are in the lowest vibrational levels of $S_n$ possible. Since the VR process is faster than electronic transitions, any excess vibrational energy is rapidly lost as the molecules are deactivated to lower vibronic levels of the corresponding excited electronic state. This excess VR energy is released as thermal energy to the surrounding medium. From the $S_n$ state, the molecule deactivates rapidly to the isoenergetic vibrational level of a lower electronic state such as $S_{n-1}$ vian internal conversion (IC) process. IC processes are transitions between states of the same multiplicity. The molecule subsequently deactivates to the lowest vibronic levels of $S_{n-1}$ via VR process. By a succession of IC processes immediately followed by VR processes, the molecule deactivates rapidly to the ground state $S_1$. This process results in excess VR and IC energy released as thermal energy to the surrounding medium leading to the overheating of the local environment surrounding the light absorbing drug molecules. The heat produced results in local cell or tissue destruction. The light absorbing species include natural chromophores in tissue or exogenous dye compounds such as indocyanine green, naphthalocyanines, and porphyrins coordinated with transition metals and metallic nanoparticles and nanoshells of metals. Natural chromophores, however, suffer from very low absorption. The choice of the exogenous photothermal agents is made on the basis of their strong absorption cross sections and highly efficient light-to-heat conversion. This feature greatly minimizes the amount of energy needed to induce local damage of the diseased cells, making therapy method less invasive.

In one embodiment of the invention, "microwave upconversion" can be used to supplement the CR-driven activation. U.S. Pat. Appl. No. 20150283392 describes up and down conversion systems for production of emitted light from various energy sources including radio frequency, microwave energy and magnetic induction sources for upconversion. The systems described therein including the plasma-gas containing capsules can be used here. For example, in this invention, This up converting "capsule" structure once in the patient or subject can be exposed to a combination of microwave energy and/or high magnetic field in order to produce light (for example UV, VIS, or IR light or a combination thereof) from the plasma gas in the gas-filled container to activate a photoactivatable drug such as psoralen. Furthermore, as described in the '392 application, the containers or capsules can include materials ("secondary electron emitters") which, upon exposure to x-rays (as from the CR radiation0 would assist in the generation of a gaseous plasma in the capsule. The '392 application describes that, when inner walls of the gas containers are coated with a material that would generate secondary electrons upon X-Ray exposure, the secondary electrons enter into high energy excitations due to radio frequency RF and/or microwave MW energy, thereby producing lower power plasma ignitions. Higher energy excitations are possible in the presence of a magnetic field.

In another embodiment, the energy source can be an internal source of radiation, often referred to as Brachytherapy. Brachytherapy involves placing radiation sources as close as possible to the tumor site. Sometimes, these sources may be inserted directly into the tumor. The radioactive sources or isotopes are in the form of wires, seeds (or molds), or rods. This technique is commonly used in treating cancers of the cervix, uterus, vagina, rectum, eye, and certain head and neck cancers. It is also occasionally used to treat cancers of the breast, brain, skin, anus, esophagus, lung, bladder, and prostate. There are several types of brachytherapy characterized by different methods of placing radiation inside the body: interstitial brachytherapy, intracavitary brachytherapy, intraluminal radiation therapy, and radioactively tagged molecules given intravenously. In some instances, brachytherapy can be combined with external beam radiation therapy to generate radiation around the treatment area with a boost of radiation delivered to the tumor area itself. The selection of radioactive seeds is known to those skilled in the art and typically based upon the anatomy of the treatment area, the energy of emission and the duration of treatment. In the present invention, these seeds can be used as the source of CR radiation or as a supplement to CR radiation.

The photoactive drug molecules can be given to a patient by oral ingestion, skin application, or by intravenous injection. The photoactive drug molecules drugs travel through the blood stream inside the body towards the targeted tumor (either via passive or active targeting strategies). The invention treatment may also be used for inducing an auto vaccine effect for malignant cells, including those in solid tumors. To the extent that any rapidly dividing cells or stem cells may be damaged by a systemic treatment, then it may be preferable to direct the stimulating energy directly toward the tumor, preventing damage to most normal, healthy cells or stem cells by avoiding photoactivation or resonant energy transfer of the photoactivatable agent.

Alternatively, a treatment may be applied that slows or pauses mitosis. Such a treatment is capable of slowing the division of rapidly dividing healthy cells or stem cells during the treatment, without pausing mitosis of cancerous cells. Alternatively, a blocking agent is administered preferentially to malignant cells prior to administering the treatment that slows mitosis.

In one embodiment, an aggressive cell proliferation disorder can be treated with CR-activation of the photoactivatable agent which has a much higher rate of mitosis, which leads to selective destruction of a disproportionate share of the malignant cells during even a systemically administered treatment. Stem cells and healthy cells may be spared from wholesale programmed cell death, even if exposed to photoactivated agents, provided that such photoactivated agents degenerate from the excited state to a lower energy state prior to binding, mitosis or other mechanisms for creating damage to the cells of a substantial fraction of the healthy stem cells.

Thus, an auto-immune response may not necessarily have to be induced.

In a further embodiment, methods in accordance with the invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A from CR is used as the activating energy, and antioxidants are added to reduce the unwanted side-effects of irradiation.

The activatable pharmaceutical agent and derivatives thereof as well as the energy modulation agent and plasmonics compounds (discussed later) and structures, can be incorporated into pharmaceutical compositions suitable for administration. Such compositions typically comprise the activatable pharmaceutical agent and a pharmaceutically acceptable carrier. The pharmaceutical composition also comprises at least one additive having a complementary therapeutic or diagnostic effect, wherein the additive is one selected from an antioxidant, an adjuvant, or a combination thereof.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such medical agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the compound of the invention to affect solubility or clearance of the compound. These molecules may also be synthesized with D-amino acids to increase resistance to enzymatic degradation. If necessary, the activatable pharmaceutical agent can be co-administered with a solubilizing agent, such as cyclodextran.

A pharmaceutical composition of the invention can be formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions (suitable for injectable use) include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (activatable drug and/or energy modulation agent) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions of the drug and/or energy modulation agent can generally include an inert diluent or an edible carrier. The oral compositions can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds (activatable drug and/or energy modulation agent) are delivered in the form of an aerosol spray from pressured container or dispenser which contains a suitable propellant, e.g., a gas such as carbon dioxide, or a nebulizer.

Systemic administration of the activatable drug and/or energy modulation agent can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds (drug and/or energy modulation agent) are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds (activatable drug and/or energy modulation agent) are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, the entire contents of which are incorporated herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, kit or dispenser together with instructions for administration.

Methods of administering agents (activatable drug and/or energy modulation agents) are not limited to the conventional means such as injection or oral infusion, but include more advanced and complex forms of energy transfer. For example, genetically engineered cells that carry and express energy modulation agents may be used. Cells from the host may be transfected with genetically engineered vectors that express bioluminescent agents. Transfection may be accomplished via in situ gene therapy techniques such as injection of viral vectors or gene guns, or may be performed ex vivo by removing a sample of the host's cells and then returning to the host upon successful transfection. Such transfected cells may be inserted or otherwise targeted at the site where diseased cells are located.

It will also be understood that the order of administering the different agents is not particularly limited. It will be appreciated that different combinations of ordering may be advantageously employed depending on factors such as the absorption rate of the agents, the localization and molecular trafficking properties of the agents, and other pharmacokinetics or pharmacodynamics considerations.

Figure 6A:
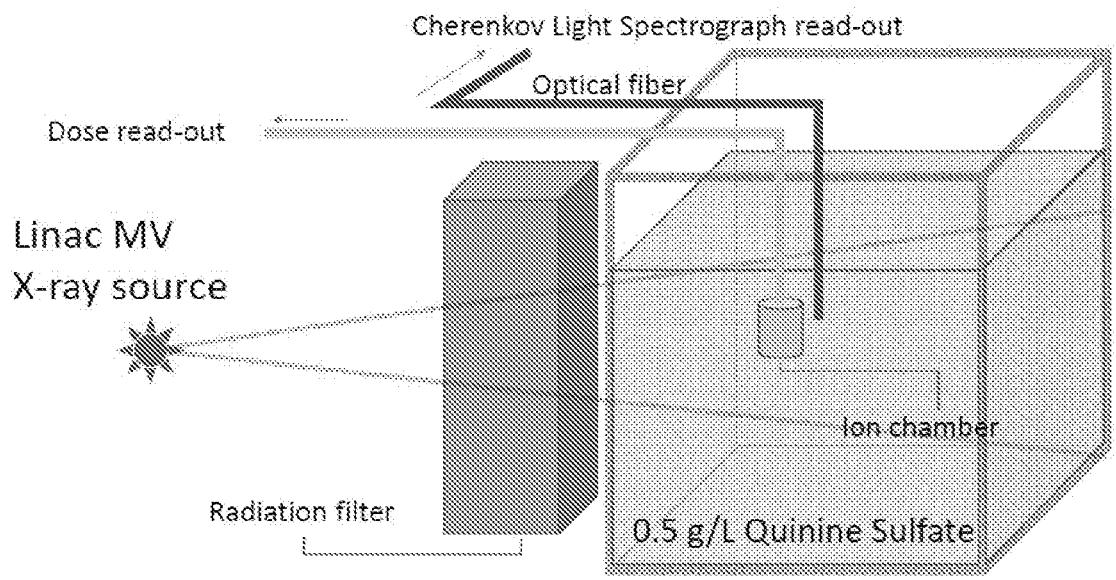
FIG. 6A is a schematic of the experimental setup used to ascertain the relative Cherenkov radiation output per x-ray dose.
Figure 6B:
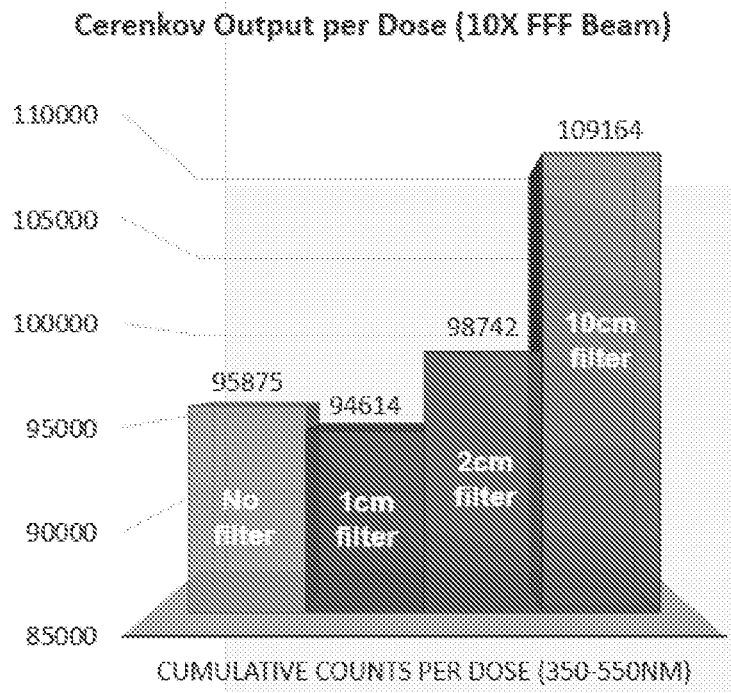
FIG. 6B is a plot of the measured Cherenkov radiation output normalized to account for differences in the total x-ray dose through different low atomic number (low atomic mass) filters.
Figure 6C:
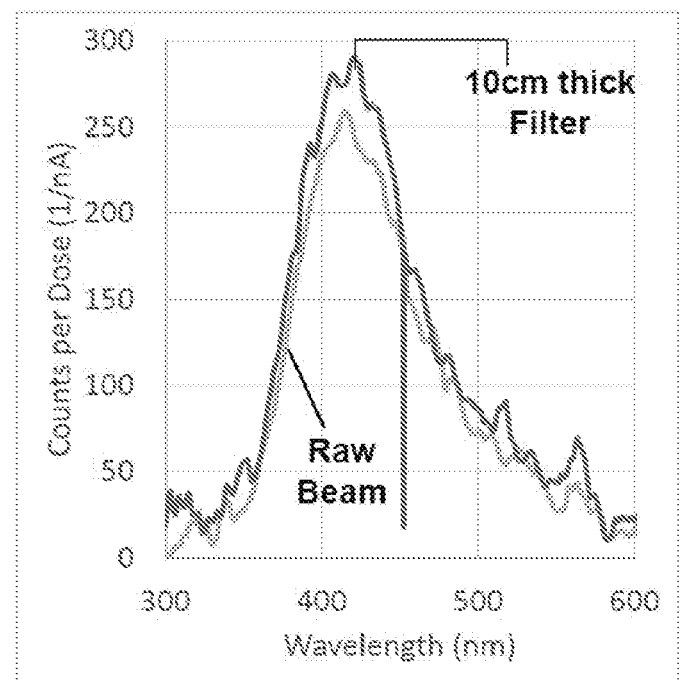
FIG. 6C is a comparison of the UV-Vis Cherenkov light spectrum with and without a 10 cm thick polyurethane filter.

An advantage of the methods of this approach is that by using x-rays to generate Cherenkov radiation (CR) light inside a diseased site and specifically target cells affected by a cell proliferation disorder, such as rapidly dividing cells, and trigger a cellular change to the cells affected by the cell proliferation disorder, such as apoptosis, in these cells in situ, whereby the immune system of the host may be stimulated to have an immune response against the diseased cells. See for example the CR light spectrum of FIG. 6C generated inside a diseased site can activate psoralen as a CR light-activated pharmaceutical agent. Once the host's own immune system is stimulated, other diseased cells that were not treated by the CR light-activated pharmaceutical agent may be recognized and destroyed by the host's own immune system. Such autovaccine effects may be obtained, for example, in treatments using psoralen and CR-activation of the psoralen using the x-ray sources and radiation filters described herein.

Another object of the invention is to treat a condition by CR-activation, disorder or disease in a subject. Exemplary conditions, disorders or diseases may include, but are not limited to, cancer, autoimmune diseases, cardiac ablasion (e.g., cardiac arrhythmiand atrial fibrillation), photoangioplastic conditions (e.g., de novo atherosclerosis, restinosis), intimal hyperplasia, arteriovenous fistula, macular degeneration, psoriasis, acne, hopeciareata, portwine spots, hair removal, rheumatoid and inflammatory arthritis, joint conditions, lymph node conditions, and cognitive and behavioral conditions.

Although not intending to be bound by any particular theory or be otherwise limited in any way, the following theoretical discussion of scientific principles and definitions are provided to help the reader gain an understanding and appreciation of the invention.

As used herein, the phrase "a disease or condition" refers to a condition, disorder or disease that may include, but are not limited to, cancer, soft and bone tissue injury, chronic pain, wound healing, nerve regeneration, viral and bacterial infections, fat deposits (liposuction), varicose veins, enlarged prostate, retinal injuries and other ocular diseases, Parkinson's disease, and behavioral, perceptional and cognitive disorders. Exemplary conditions also may include nerve (brain) imaging and stimulation, a direct control of brain cell activity with light, control of cell death (apoptosis), and alteration of cell growth and division.

As used here, the term "target structure" refers to an eukaryotic cell, prokaryotic cell, a subcellular structure, such as a cell membrane, a nuclear membrane, cell nucleus, nucleic acid, mitochondria, ribosome, or other cellular organelle or component, an extracellular structure, virus or prion, and combinations thereof.

The nature of the predetermined cellular change induced by the CR radiation will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, regulation of cytochrome c oxidase and flavoproteins, activation of mitochondria, stimulation antioxidant protective pathway, modulation of cell growth and division, alteration of firing pattern of nerves, alteration of redox properties, generation of reactive oxygen species, modulation of the activity, quantity, or number of intracellular components in a cell, modulation of the activity, quantity, or number of extracellular components produced by, excreted by, or associated with a cell, or a combination thereof. Predetermined cellular changes may or may not result in destruction or inactivation of the target structure.

In an additional embodiment, the photoactivatable agent can be a photocaged complex having an active agent contained within a photocage. The active agent can bulked up with other molecules that prevent it from binding to specific targets, thus masking its activity. When the photocage complex is photoactivated by CR and/or light from the energy modulation agents, the bulk falls off, exposing the active agent. In such a photocage complex, the photocage molecules can be photoactive (i.e. when photoactivated, they are caused to dissociate from the photocage complex, thus exposing the active agent within), or the active agent can be the photoactivatable agent (which when photoactivated causes the photocage to fall off), or both the photocage and the active agent are photoactivated, with the same or different wavelengths. For example, a toxic chemotherapeutic agent can be photocaged, which will reduce the systemic toxicity when delivered. Once the agent is concentrated in the tumor, the agent is irradiated with an activation energy. This causes the "cage" to fall off, leaving a cytotoxic agent in the tumor cell. Suitable photocages include those disclosed by Young and Deiters in "Photochemical Control of Biological Processes", *Org. Biomol. Chem.,* 5, pp. 999-1005 (2007) and "Photochemical Hammerhead Ribozyme Activation", *Bioorganic & Medicinal Chemistry Letters,* 16(10), pp. 2658-2661 (2006), the contents of which are hereby incorporated by reference.

In one embodiment, the use of CR light for uncaging a compound or agent is used for elucidation of neuron functions and imaging, for example, two-photon glutamine uncaging (Harvey C D, et al., Nature, 450:1195-1202 (2007); Eder M, et al., Rev. Neurosci., 15:167-183 (2004)). Other signaling molecules can be released by UV light stimulation, e.g., GABA, secondary messengers (e.g., $Ca^{2+}$ and $Mg^{2+}$), carbachol, capsaicin, and ATP (Zhang F., et al., 2006). Chemical modifications of ion channels and receptors may be carried out to render them light-responsive. $Ca^{2+}$ is involved in controlling fertilization, differentiation, proliferation, apoptosis, synaptic plasticity, memory, and developing axons. In yet another preferred embodiment, $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

Genetic targeting allows morphologically and electrophysipologically characterization of genetically defined cell populations. Accordingly, in an additional embodiment, a light-sensitive protein is introduced into cells or live subjects via number of techniques including electroporation, DNA microinjection, viral delivery, liposomal transfection, creation of transgenic lines and calcium-phosphate precipitation. For example, lentiviral technology provides a convenient combination a conventional combination of stable long-term expression, ease of high-titer vector production and low immunogenicity. The light-sensitive protein may be, for example, channelrhodopsin-2 (ChR2) and chloride pump halorhodopsin (NpHR). The light protein encoding gene(s) along with a cell-specific promoter can be incorporated into the lentiviral vector or other vector providing delivery of the light-sensitive protein encoding gene into a target cell. ChR2 containing a light sensor and a cation channel, provides electrical stimulation of appropriate speed and magnitude to activate neuronal spike firing, when the cells harboring Ch2R are pulsed with light.

In one embodiment, a lanthanide chelate capable of intense luminescence and excited by CR light can be used. For example, a lanthanide chelator may be covalently joined to a coumarin or coumarin derivative or a quinolone or quinolone-derivative sensitizer. Sensitizers may be a 2- or 4-quinolone, a 2- or 4-coumarin, or derivatives or combinations of these examples. A carbostyril 124 (7-amino-4-methyl-2-quinolone), a coumarin 120 (7-amino-4-methyl-2-coumarin), a coumarin 124 (7-amino-4-(trifluoromethyl)-2-coumarin), aminoinethyltrimethylpsoralen or other similar sensitizer may be used. Chelates may be selected to form high affinity complexes with lanthanides, such as terbium or europium, through chelator groups, such as DTPA. Such chelates may be coupled to any of a wide variety of probes or carriers, and may be used for resonance energy transfer to a psoralen or psoralen-derivative, such as 8-MOP, or other photoactive molecules capable of binding DNA. In one alternative example, the lanthanide chelate is localized at the site of the disease using an appropriate carrier molecule, particle or polymer, and a source of electromagnetic energy is introduced by minimally invasive procedures to irradiate the target structure, after exposure to the lanthanide chelate and a photoactive molecule.

In another embodiment, a biocompatible, endogenous fluorophore emitter can be selected to stimulate resonance energy transfer from the CR light to a photoactivatable molecule. A biocompatible emitter (e.g. the phosphors or scintillators) with an emission maxima within the absorption range of the biocompatible, endogenous fluorophore emitter may be selected to stimulate an excited state in fluorophore emitter. One or more halogen atoms may be added to any cyclic ring structure capable of intercalation between the stacked nucleotide bases in a nucleic acid (either DNA or RNA) to confer new photoactive properties to the intercalator. Any intercalating molecule (psoralens, coumarins, or other polycyclic ring structures) may be selectively modified by halogenation or addition of non-hydrogen bonding ionic substituents to impart advantages in its reaction photochemistry and its competitive binding affinity for nucleic acids over cell membranes or charged proteins, as is known in the art.

In various embodiments, the initiation energy source may be a linear accelerator equipped with at least kV image guided computer-control capability to deliver a precisely calibrated beam of radiation to a pre-selected coordinate. One example of such linear accelerators is the SMART-BEAM™ IMRT (intensity modulated radiation therapy) system (from Varian Medical Systems, Inc., Palo Alto, Calif.) or Varian OBI technology (OBI stands for "On-board Imaging", and is found on many commercial models of Varian machines). In other embodiments, the initiation energy source may be commercially available components of X-ray machines or non-medical X-ray machines. X-ray machines that produce from 10 to 150 keV X-rays are readily available in the marketplace. For instance, the General Electric DEFINIUM series or the Siemens MULTIX series are two non-limiting examples of typical X-ray machines designed for the medical industry, while the EAGLE PACK series from Smith Detection is an example of a non-medical X-ray machine. Another suitable commercially available device is the SIEMENS DEFINITION FLASH, (a CT system), by Siemens Medical Solutions. As such, the invention is capable of performing its desired function when used in conjunction with commercial X-ray equipment. Current medical linear accelerators produce high energy electron and photon beams in the energy range 6-20 MeV. The threshold energy for Cherenkov production is ~0.8 MeV, with higher energies producing more Cherenkov radiation inside the medium.

Computer-Assisted Control

Figure 3:
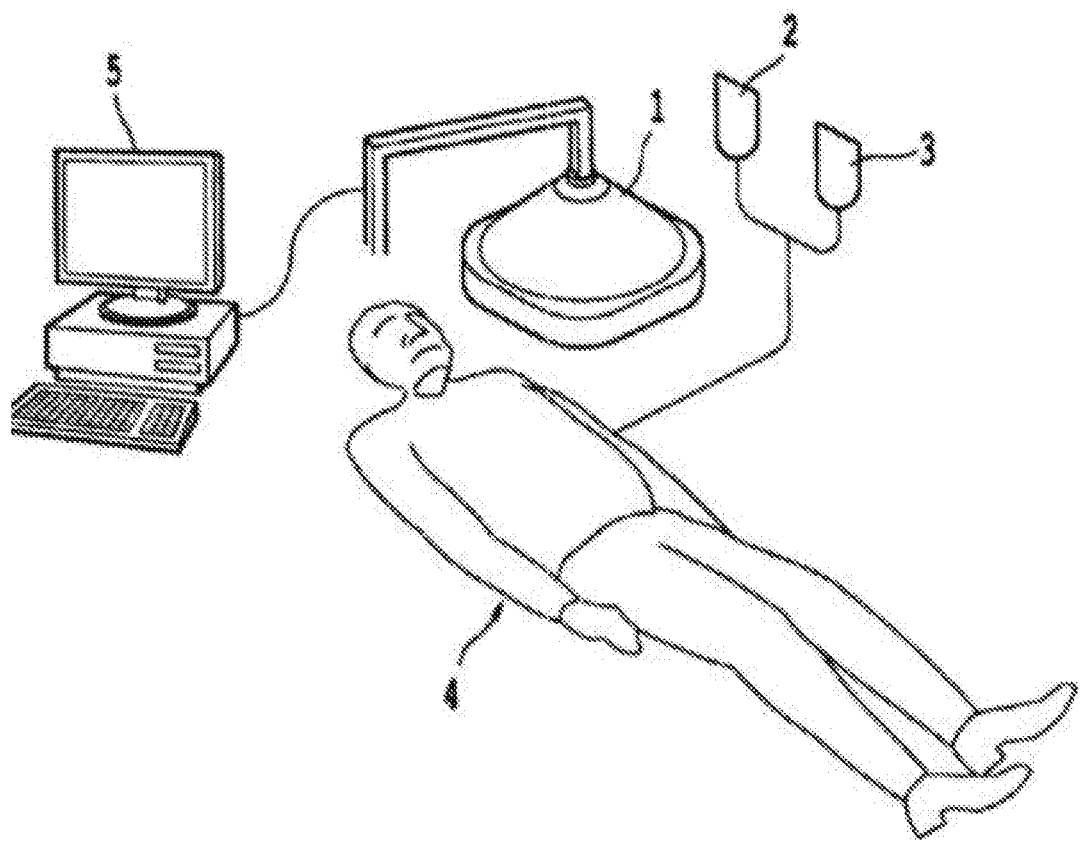
FIG. 3 is a schematic of a system according to one exemplary embodiment of the invention.

FIG. 3 illustrates a system according to one exemplary embodiment of the invention. Referring to FIG. 3, an exemplary system according to one embodiment of the invention may have an initiation energy source 1 directed at the subject 4. An activatable pharmaceutical agent 2 and an energy modulation agent 3 can be administered to the subject 4. The initiation energy source may additionally be controlled by a computer system 5 that is capable of directing the delivery of the initiation energy (e.g., X-rays).

In further embodiments, dose calculation and robotic manipulation devices (such as the CYBER-KNIFE robotic radiosurgery system, available from Accuray, or similar types of devices) may also be included in the system to adjust the distance between the initiation energy source 1 and the subject 4 and/or to adjust the energy and/or dose of the initiation energy source such that the x-rays incident on the target site are within an energy band bounded by a lower energy threshold capable of inducing desirable reactions and an upper energy threshold leading to denaturization of the medium. Further refinements in the x-ray energy and dose can be had by adjusting the distance to the subject 5 or the intervening materials between the target site and the initiation energy source 1.

In another embodiment, there is also provided a computer implemented system for designing and selecting suitable combinations of initiation energy source, energy transfer agent, and activatable pharmaceutical agent, comprising:

a central processing unit (CPU) having a storage medium on which is provided:

a database of excitable compounds;

a first computation module for identifying and designing an excitable compound (e.g., a photoactivatable drug) that is capable of binding with a target cellular structure or component; and a second computation module predicting the initiation energy and dose producing the CR light needed for excitation of the excitable compound, wherein the system, upon selection of a target cellular structure or component, computes an excitable compound that is capable of interacting with the target structure.

The computer-implemented system according to one embodiment of the invention may have a central processing unit (CPU) connected to a memory unit, configured such that the CPU is capable of processing user inputs and selecting a combination of initiation source (or initiation energies or distances), activatable pharmaceutical agent, and energy modulation or energy transfer agents for use in a method of the invention.

The computer-implemented system according to one embodiment of the invention includes (or is programmed to act as) an x-ray source (or high energy source such as an electron beam) control device configured to calculate an x-ray (radiation) exposure condition including a distance between the initiation energy source 1 and the subject 4 and the energy band bounded by the above-noted lower energy threshold capable of inducing desirable reactions and the above-noted upper energy threshold leading to denaturization of the medium. The control device operates the x-ray or high energy source (the initiation energy source 1) within the exposure condition to provide a requisite energy and/or dose of x-rays to the subject or a target site of the subject.

In one embodiment of the invention, there is provided a computer implemented system for designing and selecting suitable combinations of initiation energy source, energy modulation agent(s), and activatable agent(s). For example, the computer system 5 shown in FIG. 3 can include a central processing unit (CPU) having a storage medium on which is provided: a database of excitable compounds, a first computation module for a photoactivatable agent or energy transfer agent, and a second computation module predicting the requisite energy flux needed to sufficiently activate the energy transfer agent or photoactivatable agent.

Figure 4:
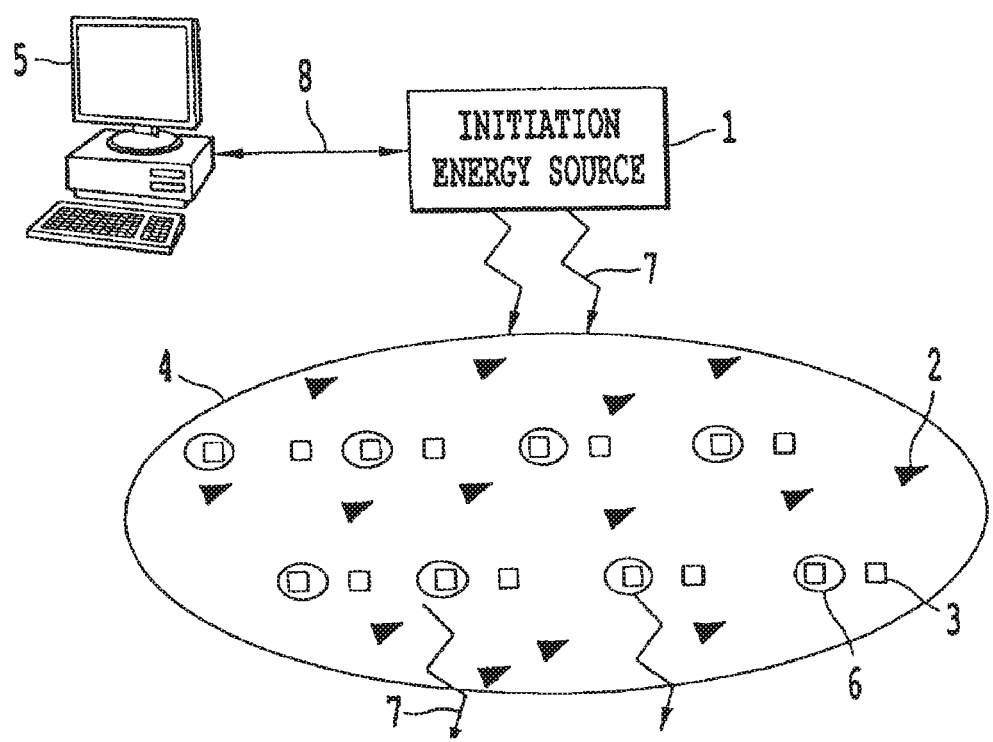
FIG. 4 is a schematic of an exemplary system according to one embodiment of the invention for treatment of a biological medium.

Referring to FIG. 4, an exemplary system according to one embodiment of the invention may have an initiation energy source 1 directed at a biological medium 4. Activatable agents 2 and an energy modulation agents 3 are dispersed throughout the biological medium 4. The initiation energy source 1 may additionally be connected via a network 8 to a computer system 5 capable of directing the delivery of the initiation energy. In various embodiments, the energy modulation agents 3 are encapsulated energy modulation agents 6, depicted in FIG. 4 as silica encased energy modulation agents. As shown in FIG. 4, initiation energy 7 in the form of radiation from the initiation energy source 1 permeated throughout the biological medium 4.

A more thorough discussion of the computer system 5 is provided below in reference to FIG. 5. As discussed below in more detail, the initiation energy source 1 can be an external energy source or an energy source located at least partially in the biological medium 4. As discussed below in more detail, activatable agents 2 and/or the energy modulation agents 3 can include plasmonics agents which enhance either the applied energy or the energy emitted from the energy modulation agents 3 so as to directly or indirectly produce a change in the biological medium.

Figure 5:
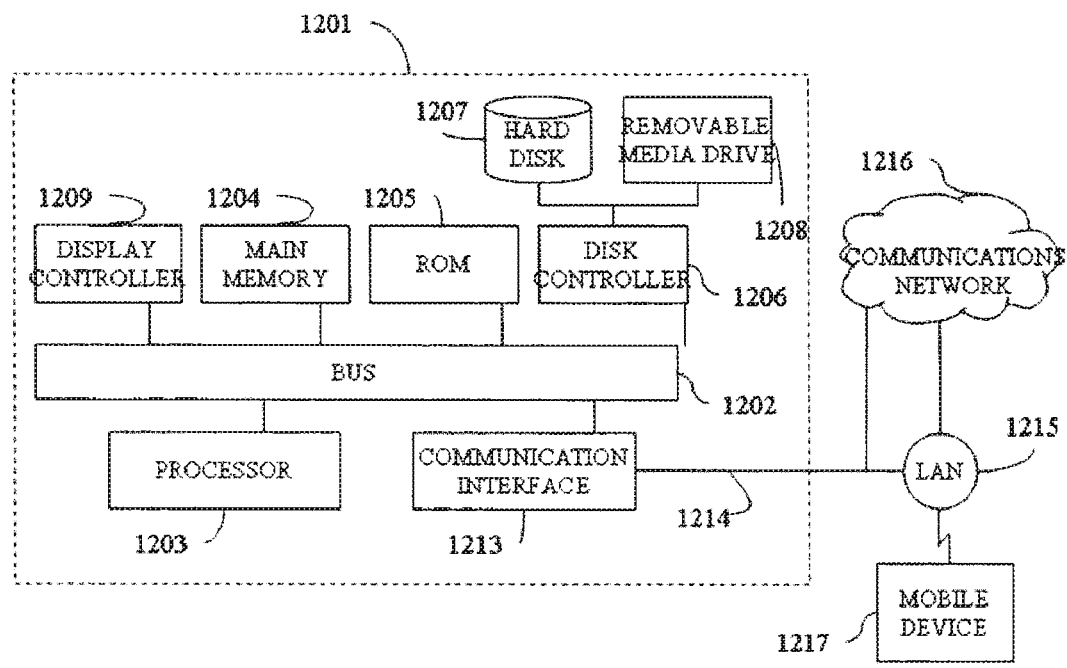
FIG. 5 is a schematic illustrating an exemplary computer system for implementing various embodiments of the invention.

FIG. 5 illustrates a computer system 1201 for implementing various embodiments of the invention. The computer system 1201 may be used as the computer system 5 to perform any or all of the functions described above. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable read only memory (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display, such as a cathode ray tube (CRT), for displaying information to a computer user. The computer system includes input devices, such as a keyboard and a pointing device, for interacting with a computer user and providing information to the processor 1203.

The pointing device, for example, may be a mouse, a trackball, or a pointing stick for communicating direction information and command selections to the processor 1203 and for controlling cursor movement on the display. In addition, a printer may provide printed listings of data stored and/or generated by the computer system 1201.

The computer system 1201 performs a portion or all of the processing steps (or functions) of this invention in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein.

Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, or other physical medium with patterns of holes, a carrier wave (described below), or any other medium from which a computer can read.

Stored on any one or on a combination of computer readable media, the invention includes software for controlling the computer system 1201, for driving a device or devices for implementing the invention, and for enabling the computer system 1201 to interact with a human user. Such software may include, but is not limited to, device drivers, operating systems, development tools, and applications software. Such computer readable media further includes the computer program product of the invention for performing all or a portion (if processing is distributed) of the processing performed in implementing the invention.

The computer code devices of the invention may be any interpretable or executable code mechanism, including but not limited to scripts, interpretable programs, dynamic link libraries (DLLs), Java classes, and complete executable programs. Moreover, parts of the processing of the invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202.

Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the invention remotely into a dynamic memory and send the instructions for example over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213. Moreover, the network link 1214 may provide a connection through a LAN 1215 to a mobile device 1217 such as a personal digital assistant (PDA) laptop computer, or cellular telephone.

The reagents and chemicals useful for methods and systems of the invention may be packaged in kits to facilitate application of the invention. In one exemplary embodiment, a kit would comprise at least one activatable agent capable of producing a predetermined cellular change, optionally at least one energy modulation agent capable of activating the at least one activatable agent when energized, optionally at least one plasmonics agent that can enhance the CR light such that the CR light activates the at least one activatable agent which produces a change in the medium when activated, and containers suitable for storing the various agents in stable form, and further comprising instructions for administering the at least one activatable agent and/or at least one energy modulation agent to a medium, and for applying an initiation energy from an initiation energy source to activate the activatable agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

System Implementation

In one embodiment, there is a system for imaging or treating a tumor in a human or animal body. The system includes a pharmaceutical carrier, a photoactivatable drug, one or more devices which infuse the tumor with the photoactivatable drug and the pharmaceutical carrier, an x-ray or high energy electron or proton source, and a processor programmed to control a dose of x-rays or electrons to the tumor for production of light inside the tumor by CR to activate the photoactivatable drug.

In one embodiment of the invention, there is a system for producing a change in a biological medium. The first system includes a mechanism configured to supply in the biological medium at least one of a plasmonics agent and a photoactivatable drug and an energy modulation agent. The plasmonics agent enhances or modifies energy in a vicinity of itself. In one example, the plasmonics agent enhances or modifies the CR such that the enhanced CR produces directly or indirectly the change in the medium. The system includes an initiation energy source configured to apply an initiation energy to the biological medium to activate the at least one activatable agent in the biological medium.

In one embodiment, the applied initiation energy or the CR interacts with the energy modulation agent to directly or indirectly produce the change in the medium by emitted light (UV and/or visible light) from the CR light or from the energy modulation agent.

In one embodiment, the energy modulation agent converts the applied initiation energy or the CR light and produces light (UV and/or visible light) at an energy to activate the drug or photoactivatable substance. The plasmonics agent (if present) can enhance the light from the at least one energy modulation agent or the CR light. In one embodiment, the applied initiation energy source is an external initiation energy source.

The systems described herein can further permit the at least one activatable agent to include a photoinitiator such as one of benzoin, substituted benzoins, alkyl ester substituted benzoins, Michler's ketone, dialkoxyacetophenones, diethoxyacetophenone, benzophenone, substituted benzophenones, acetophenone, substituted acetophenones, xanthone, substituted xanthones, benzoin methyl ether, benzoin ethyl ether, benzoin isopropyl ether, diethoxyxanthone, chloro-thio-xanthone, azo-bisisobutyronitrile, N-methyl diethanolaminebenzophenone, camphoquinone, peroxyester initiators, non-fluorene-carboxylic acid peroxyesters and mixtures thereof.

The systems described herein can also include a mechanism configured to provide in the medium plasmonics-agents including metal nanostructures such as for example nanospheres, nanorods, nanocubes, nanopyramids, nanoshells, multi-layer nanoshells, and combinations thereof.

Accordingly, radiation produced from the energy modulation agent or CR can also be enhanced by the plasmonics agents in the medium. The article can include luminescent particles such as for example nanotubes, nanoparticles, chemiluminescent particles, and bioluminescent particles, and mixtures thereof. The article can include nanoparticles of semiconducting or metallic materials. The article can include chemiluminescent particles. The article can include plasmonics-agents including metal nanostructures such as for example nanospheres, nanorods, nanocubes, nanopyramids, nanoshells, multi-layer nanoshells, and combinations thereof.

Treatment of Cell-Proliferation Disorders

In a preferred embodiment of the invention, a subject is administered an activatable pharmaceutical agent, optionally along with at least one energy modulation agent capable of converting x-rays into a wavelength that will activate the activatable pharmaceutical agent. The subject is then placed into a source of x-rays or high energy particles which generate inside the subject CR. From the CR light, at least one photoactive drug is activated inside the subject to thereby treat the subject for a cell proliferation disorder.

Alternatively, or in addition, another aspect of the invention includes a method for treating a subject carrying a virus in which the method provides within the subject at least one photoactive drug for treatment of the subject carrying the virus and applies initiation energy from at least one source to a target inside the subject. The at least one photoactive drug is activated directly or indirectly at the target inside the subject by CR light or light from energy modulation agents to thereby treat the subject carrying the virus.

Mechanisms included in the invention can involve photoactivation of a drug such as a psoralen or its derivatives or an alkylating agent. Mechanisms included in the invention can involve the formation of highly reactive oxygen species, such as singlet oxygen. Any of these mechanisms can be used in combination or selectively to treat a subject with a cell proliferation disorder, or who is carrying viruses and/or has associated disorders or symptoms thereof. In one embodiment, the CR light can be used to activate an alkylating agent (e.g., iodonophthylazide) for its attachment to a virus. In one embodiment, the CR light can be used to activate a psoralen (or a derivative or substitute thereof) for treatment of a bacterial infection or other disorders in the patient. In one embodiment, one wavelength of the CR light can be used to activate an alkylating agent (e.g., iodonophthylazide) for its attachment to a virus, while another different wavelength of the CR light can be used to activate a psoralen (or a derivative or substitute thereof) for treatment of a bacterial infection or other disorders in the patient. In one embodiment, one wavelength can be used to activate an alkylating agent or a psoralen, while another wavelength is used for a different purpose such as for example production of singlet oxygen (i.e., highly reactive oxygen species) or for production of sterilizing UV light or to promote cell growth or reduce inflammation, etc.

In various embodiments, one or more wavelengths of the CR light could be used for treatment a host or arrest of viruses such as Ebola, West Nile, encephalitis, HIV, etc., and/or for the regulation and control of biological responses having varying degrees of apoptosis (the process of programmed cell death PCD) and necrosis (the premature death of cells and living tissue typically from external factors). In necrosis, factors external to the cell or tissue, such as infection, toxins, or trauma that result in the unregulated digestion of cell components. In contrast, apoptosis is a naturally occurring programmed and targeted cause of cellular death. While apoptosis often provides beneficial effects to the organism, necrosis is almost always detrimental and may be fatal.

In various embodiments of this invention, the alkylating agent can be at least one or more of drugs from the iodonophthylazide family, such as 1,5-iodonaphthylazide (INA). These photoactivatable compounds are non-toxic, hydrophobic compounds that can penetrate into the innermost regions of biological membrane bilayers and selectively accumulate in such inner membrane regions. Upon irradiation with CR light or light from energy modulation agents, generated inside or nearby the membrane region, it is believed that a reactive derivative of the compound is generated that binds to membrane proteins deep in the lipid bilayer. This process would (similar to that in the '602 patent) inactivate integral membrane proteins embedded in the membrane while maintaining the structural integrity and activity of the proteins that protrude from the extracellular surface of the membrane. In one aspect of the invention, the inactivated agent constitutes a vaccine created inside the subject animal or bird or human with the vaccine specific to the viral or bacterial infection of the animal or bird or human.

In various embodiments of this invention, a photoactive drug such as a psoralen or its derivatives is used separately or in conjunction with at least one alkylating agent. When using a psoralen, the psoralen is photactivated inside the cell by ultraviolet or visible light generated within the cell or nearby the cell by the CR light or by light from energy modulation agents. The activated psoralen attaches to the virus's genetic contents, prevents its replication, and causes local cell death (one form of treatment). Alternatively or in addition, the psoralen-inactivated virus can induce an autoimmune response from the animal or bird or human resulting in the body effectively eliminating untreated viruses in other regions of the body.

In one embodiment of the invention, 1,5-iodonaphthyl azide (INA) is employed as a photoactivatable hydrophobic compound. INA is a nontoxic hydrophobic compound. The structure for 1,5-iodonaphthyl azide (INA) is provided below.

Upon exposure to cells, the photoactivatable hydrophobic compounds can penetrate into the innermost regions of biological membrane bilayers and will accumulate selectively in these regions. Upon irradiation with ultraviolet light (e.g., 320 to 400 nm) generated (or otherwise provided) internally within the animal or bird or human subject by the CR light or light from energy modulation agents, it is believed that a reactive derivative is generated that binds to membrane proteins deep in the lipid bilayer.

In another embodiment of the invention, the photoactivatable hydrophobic compounds of the invention can be used for inactivation of viruses, bacteria, parasites and tumor cells using visible light. However, when visible light is used a photosensitizer, a chromophore is typically needed unless the photoactive drug is developed to be activated directly by visible light. A photosensitizer chromophore has an absorption maximum in the visible light range and can photosensitize the photoactivatable hydrophobic compounds of the invention. In general, the photosensitizer chromophores have absorption maxima in the range of about 450 to about 525 nm or about 600 to about 700 nm. Suitable photosensitizer chromophores can include one or more of a porphyrin, chlorin, bacteriochlorin, purpurin, phthalocyanine, naphthalocyanine, merocyanines, carbocyanine, texaphyrin, non-tetrapyrrole, or other photosensitizers known in the art. Specific examples of photosensitizer chromophores include fluorescein, eosin, bodipy, nitro-benzo-diazol (NBD), erythrosine, acridine orange, doxorubicin, rhodamine 123, picoerythrin and the like.

As provided in various embodiments of the invention, viruses, bacteria, parasites and tumor cells and other infectious structures and microorganisms can be inactivated by exposure to photoactivatable hydrophobic compounds which were themselves activated by light generated internally within the animal or bird or human subject by CR light or light from energy modulation agents or light from photosensitizer chromophores. In various embodiments, the photoactivatable hydrophobic compound is 1,5-iodonaphthyl azide (INA) or a related compound. In one embodiment of the invention, the virus, parasite or tumor cell is contacted with the recently photoactivated hydrophobic compound, which was photoactivated by ultraviolet light generated internally using the energy modulation agents of the invention. If the virus, parasite, tumor cell or other infectious structures and microorganisms are contacted with both the photoactivatable hydrophobic compound and a photosensitizer chromophore that absorbs visible light, then visible light generated internally by CR light or light from energy modulation agents or light from photosensitizer chromophores can photoactivate the photoactivatable hydrophobic compound. Accordingly, in one embodiment, exposure to internally generated ultraviolet light directly photoactivates the photoactivatable hydrophobic compound within viral and cellular membranes. In one embodiment, exposure to internally generated visible light first photoactivates the photosensitizer chromophore, which then activates or photosensitizes the photoactivatable hydrophobic compound within viral or cellular membranes.

In either case, a reactive derivative of the photoactivatable hydrophobic compound is generated that binds to membrane proteins deep within the lipid bilayer. This process is believed to cause specific inactivation of integral membrane proteins embedded in the membrane, while maintaining the integrity and activity of proteins that protrude outside of the membrane.

The invention with internally generated light can provide a method that can inactivate a wide variety of viruses, bacteria, parasites and tumor cells in a way that the inactivated species can be safely used as immunological compositions or vaccines to inhibit the disease they cause. The activated drug agents (generated indirectly from the CR light activating a photoactivatable drug) kill the organism or cell in a specific manner that maintains its structure and conformation. Hence, the structure of the inactivated virus/cell is similar to that of the live virus/cell. In this way, the immunogenicity of the organism or cell as a whole is maintained and can be safely used to stimulate the immune system of a subject animal or bird or patient. Similarly, in one aspect of the invention, the inactivated viruses, bacteria, cancer cells, or parasites generated inside the animal or bird or human subject can be used for vaccination without causing disease or other negative side effects.

Hence, the INA internal treatment procedures generate inactive viruses inside the subject that can be used in a manner similar to aldrithiol inactivated HIV (developed by the AIDS vaccine program SAIC). Alternatively, the INA-internal-inactivation procedures of this invention can be used in conjunction with aldrithiol inactivation procedures to generate inactive HIV that comply with the requirements of the FDA. Thus, in one aspect of this invention, two mechanistically independent methods of inactivation can be used to provide a prophylactic AIDS or HIV vaccine.

In one aspect of the invention, prevention or treatment of microbial infections, viral infections, parasitic infections, prion infection or cancer is intended to include the alleviation of or diminishment of at least one symptom typically associated with the infection or cancer. Prevention or treatment also includes alleviation or diminishment of more than one symptom. Ideally, treatment with the internally inactivated agents of the invention generates immunity in the animal or bird or human towards the agent while prevention by the inactivated agents of the invention substantially eliminates the symptoms associated with the infection or cancer.

In various embodiments of the invention, infections that can be treated by the present internally activated drug agents (generated indirectly from the CR light activating a photoactivatable drug) include infections by any target infectious organisms and structures that can infect a mammal or other animal or a bird. Such target infectious organisms and structures include, but are not limited to, any virus, bacterium, fungus, single cell organism, prion conformations or parasite that can infect an animal, including mammals. For example, target microbial organisms include viruses, bacteria, fungi, yeast strains and other single cell organisms. In another embodiment, the inactivated agents of the invention can give rise to immunity against both gram-negative and gram-positive bacteria.

Exemplary viral infections that can be treated by this invention include infections by any virus that can infect animals (including but not limited to mammals or birds), including enveloped and non-enveloped viruses, DNA and RNA viruses, viroids, and prions. Hence, for example, infections or unwanted levels of the following viruses and viral types can be treated internally: human immunodeficiency virus (HIV), simian immunodeficiency virus (SIV), hemorrhagic fever viruses, hepatitis A virus, hepatitis B virus, hepatitis C virus, poxviruses, herpes viruses, adenoviruses, papovaviruses, parvoviruses, reoviruses, orbiviruses, picornaviruses, caliciviruses, alphaviruses, rubiviruses, influenza virus type A and B, flaviviruses, coronaviruses, paramyxoviruses, morbilliviruses, pneumoviruses, rhabdoviruses, lyssaviruses, orthmyxoviruses, bunyaviruses, phleboviruses, nairoviruses, hepadnaviruses, arenaviruses, retroviruses, enteroviruses, rhinoviruses and the filovirus.

Infections or unwanted levels of the following target viruses and viral types that are believed to have potential as biological weapons can be treated, prevented or addressed by the internally inactivated agents of this invention: hemorrhagic fever viruses (HFVs), Chikungunya virus, Japanese encephalitis virus, Monkey pox virus, variola virus, Congo-Crimean hemorrhagic fever virus, Junin virus, Omsk hemorrhagic fever virus, Venezuelan equine encephalitis virus, Dengue fever virus, Lassa fever virus, Rift valley fever virus, Western equine encephalitis virus, Eastern equine encephalitis virus, Lymphocytic choriomeningitis virus, Russian Spring-Summer encephalitis virus, White pox, Ebola virus, Machupo virus, Smallpox virus, Yellow fever virus, Hantaan virus, Marburg virus, and Tick-borne encephalitis virus.

Similarly, infections or unwanted levels of the following examples of target microbial organisms can be treated by this invention: *Aeromonas* spp. (including, for example, *Aeromonas hydrophila, Aeromonas caviae* and *Aeromonas sobria*), *Bacillus* spp. (including, for example, *Bacillus cereus, Bacillus anthracis* and *Bacillus thuringiensis*), *Bacteroides* spp. (including, for example, *B. fragilis, B. thetaiotaomicron, B. vulgatus, B. ovatus, B. distasonis, B. uniformis, B. stercoris, B. eggerthii, B. merdae*, and *B. caccae*), *Campylobacter* spp. (including, for example, *Campylobacter jejuni, Campylobacter laridis*, and *Campylobacter hyointestinalis*), *Clostridium* spp. (such as the pathogenic clostridia including all types of *Clostridium botulinum* (including those in Groups I, II, III and IV, and including those that produce botulism A, B, C, D, E, F and G), all types of *Clostridium tetani*, all types of *Clostridium difficile*, and all types of *Clostridium perfringens*), Ebola spp. (e.g. EBOV Zaire), *Enterobacter* spp. (including, for example, *Enterobacter aerogenes* (also sometimes referred to as *Klebsiella mobilis*), *Enterobacter agglomerans* (also sometimes referred to as *Pantoea agglomerans*), *Enterobacter amnigenus, Enterobacter asburiae, Enterobacter cancerogenus* (also sometimes referred to as *Enterobacter taylorae* and/or *Erwinia cancerogena*), *Enterobacter cloacae, Enterobacter cowanii, Enterobacter dissolvens* (also sometimes referred to as *Erwinia dissolvens*), *Enterobacter gergoviae, Enterobacter hormaechei, Enterobacter intermedium, Enterobacter intermedius* (also sometimes referred to as *Enterobacter intermedium*), *Enterobacter kobei, Enterobacter nimipressuralis* (also sometimes referred to as *Erwinia nimipressuralis*), *Enterobacter sakazakii*, and *Enterobacter taylorae* (also sometimes referred to as *Enterobacter cancerogenus*)), *Enterococcus* spp. (including, for example, Vancomycin Resistant *Enterococcus* (VRE), *Enterococcus faecalis, Enterococcus faecium, Enterococcus durans, Enterococcus gallinarum*, and *Enterococcus casseliflavus*), *Escherichia* spp. (including the enterotoxigenic (ETEC) strains, the enteropathogenic (EPEC) strains, the enterohemorrhagic (EHEC) strain designated *E. coli* O157:H7, and the enteroinvasive (EIEC) strains), *Gastrospirillum* spp. (including, for example, *Gastrospirillum hominis* (also sometimes now referred to as *Helicobacter heilmannii*), *Helicobacter* spp. (including, for example, *Helicobacter pylori* and *Helicobacter hepaticus*), *Klebsiella* spp. (including, for example, *Klebsiella pneumoniae, Klebsiella ozaenae, Klebsiella rhinoscleromatis, Klebsiella oxytoca, Klebsiella planticola, Klebsiella terrigena*, and *Klebsiella ornithinolytica*), *Salmonella* spp. (including, for example, *S. typhi* and *S. paratyphi* A, B, and C, *S. enteritidis*, and *S. dublin*), *Shigella* spp. (including, for example, *Shigella sonnei, Shigella boydii, Shigella flexneri*, and *Shigella dysenteriae*), *Staphylococcus* spp. (including, for example, *Staphylococcus aureus*, methicillin-resistant *Staphylococcus aureus* (MRSA), *Staphylococcus saprophyticus* and *Staphylococcus epidermis*), *Streptococcus* ssp. (including Groups A (one species with 40 antigenic types, *Streptococcus pyogenes*), B, C, D (five species (*Streptococcus faecalis, Streptococcus faecium, Streptococcus durans, Streptococcus avium*, and *Streptococcus bovis*)), F, and G, including *Streptococcus pneumoniae*), *Pseudomonas* spp. (including, for example, *Pseudomonas aeruginosa, Pseudomonas maltophilia, Pseudomonas fluorescens, Pseudomonas putida, Pseudomonas cepacia, Pseudomonas stutzeri, Pseudomonas mallei, Pseudomonas pseudomallei* and *Pseudomonas putrefaciens*), *Vibrio* spp. (including, for example, *Vibrio cholera* Serogroup O1 and *Vibrio cholera* Serogroup Non-O1, *Vibrio parahaemolyticus*, 5 *Vibrio alginolyticus, Vibrio furnissii, Vibrio carchariae, Vibrio hollisae, Vibrio cincinnatiensis, Vibrio metschnikovii, Vibrio damsela, Vibrio mimicus, Vibrio vulnificus*, and *Vibrio fluvialis*), *Yersinia* spp. (including, for example, *Yersinia pestis, Yersinia enterocolitica* and *Yersinia pseudotuberculosis*), *Neisseria, Proteus, Citrobacter, Aerobacter, Providencia, Serratia, Brucella, Francisella tularensis* (also sometimes referred to as *Pasteurella tularensis, Bacillus tularensis, Brucella tularensis*, tularemia, rabbit fever, deerfly fever, Ohara's disease, and/or Francis disease), and the like.

Thus, for example, various bacterial infections or unwanted levels of bacteria that can be treated, prevented or addressed by the present invention include but are not limited to those associated with anthrax (*Bacillus anthracis*), staph infections (*Staphylococcus aureus*), typhus (*Salmonella typhi*), food poisoning (*Escherichia coli*, such as O157:H7), bascillary dysentery (*Shigella* dysenteria), pneumonia (Psuedomonas aerugenosa and/or *Pseudomonas cepacia*), cholera (*Vibrio cholerae*), ulcers (*Helicobacter pylori*), *Bacillus cereus, Salmonella, Clostridium perfringens, Campylobacter, Listeria monocytogenes, Vibrio parahaemolyticus*, botulism (*Clostridium botulinum*), smallpox (variola major), listeriosis (*Listeria monocytogenes*), tularemia (*Francisella tularensis*), plague (*Yersinia pestis*; also sometimes referred to as bubonic plague, pneumonic plague, and/or black death) and others. *E. coli* serotype O157:H7 has been implicated in the pathogenesis of diarrhea, hemorrhagic colitis, hemolytic uremic syndrome (HUS) and thrombotic thrombocytopenic purpura (TTP). As indicated herein, the internally inactivated agents of this invention are also active against drug-resistant and multiply-drug resistant strains of bacteria, for example, multiply-resistant strains of *Staphylococcus aureus* and vancomycin-resistant strains of *Enterococcus faecium* and *Enterococcus faecalis*.

Fungal infections that can be treated or prevented by this invention include infections by fungi that infect a mammal or a bird, including *Histoplasma capsulatum, Coccidioides immitis, Cryptococcus neoformans, Candida* ssp. including *Candida albicans, Aspergilli* ssp. including *Aspergillus fumigatus, Sporothrix, Trichophyton* ssp., *Fusarium* ssp., *Tricosporon* ssp., *Pneumocystis carinii*, and *Trichophyton mentagrophytes*. Hence, for example, infections or unwanted levels of target fungi can be treated, prevented or addressed by the present inactivated agents. Such fungi also include fungal pathogens that may have potential for use biological weapons, including *Coccidioides immitis* and *Histoplasma capsulatum*.

Figure 7A:
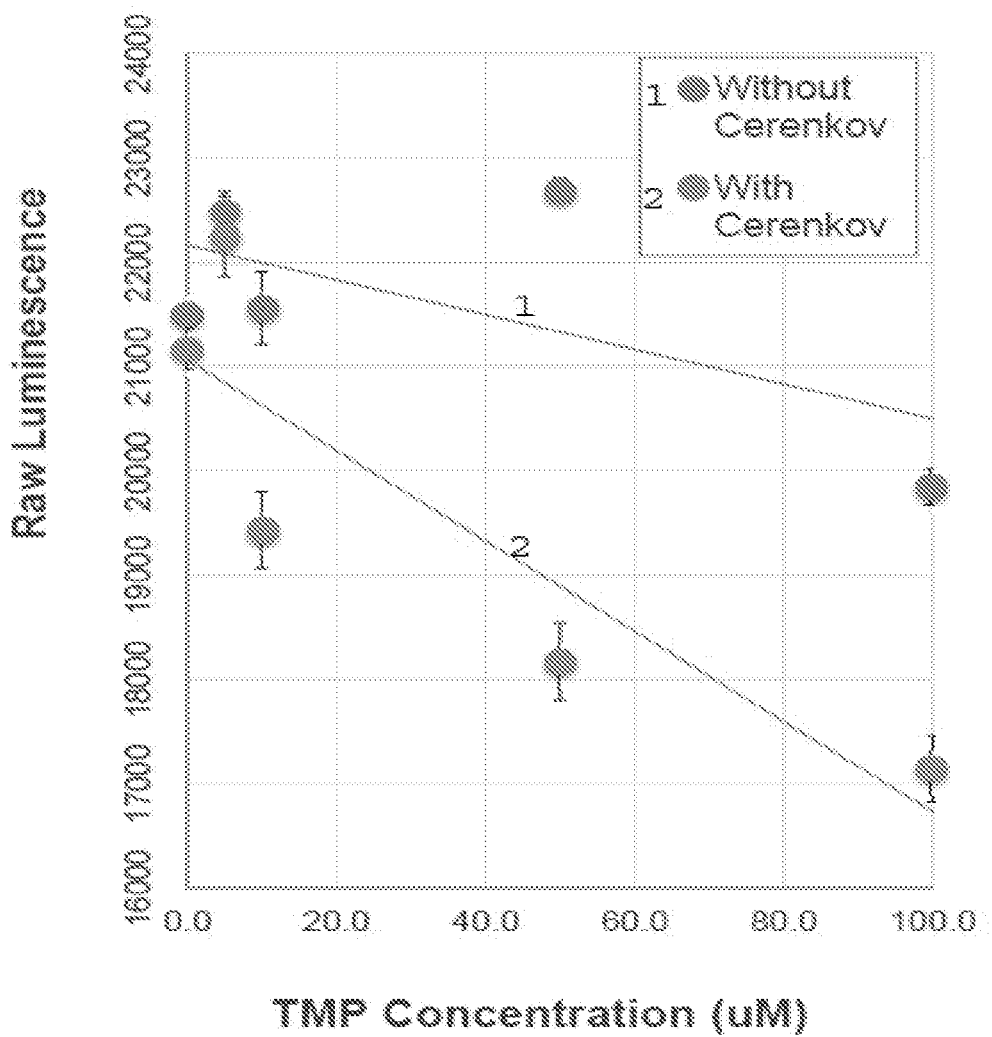
FIG. 7A is a plot of cell kill as a function of TMP concentration with and without exposure to UV-Vis Cherenkov light.
Figure 7B:
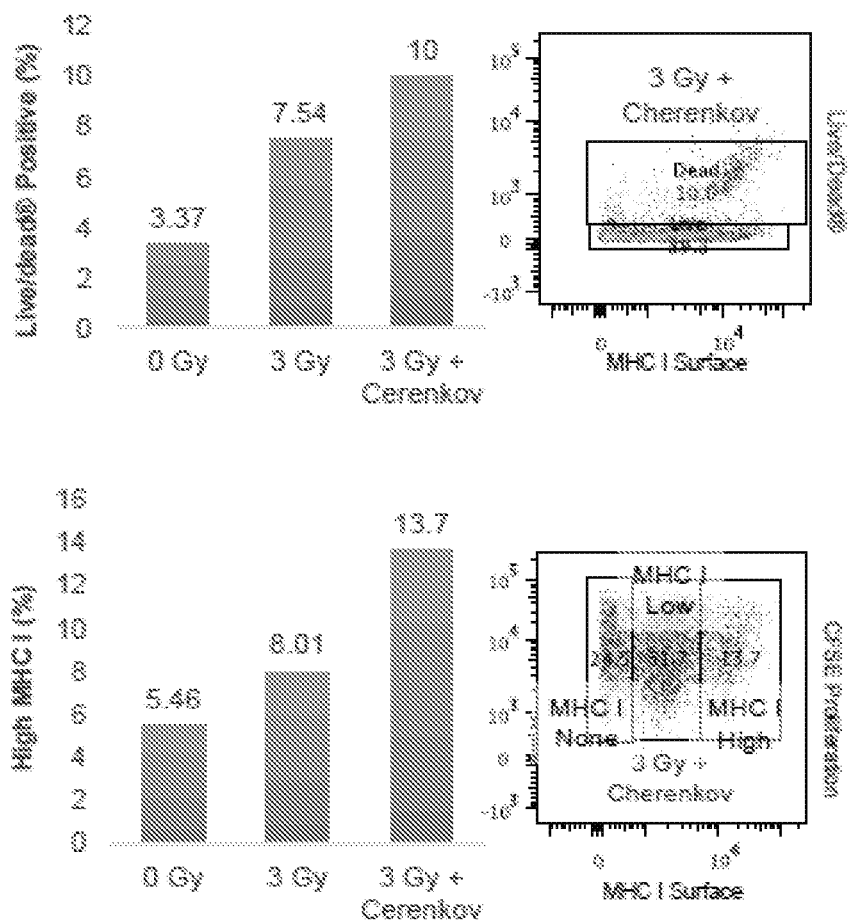
FIG. 7B is a plot of the flow cytometry data acquired from B16 melanoma cells indicating a similar effect to the cytotoxicity depicted in FIG. 7A.
Figure 7C:
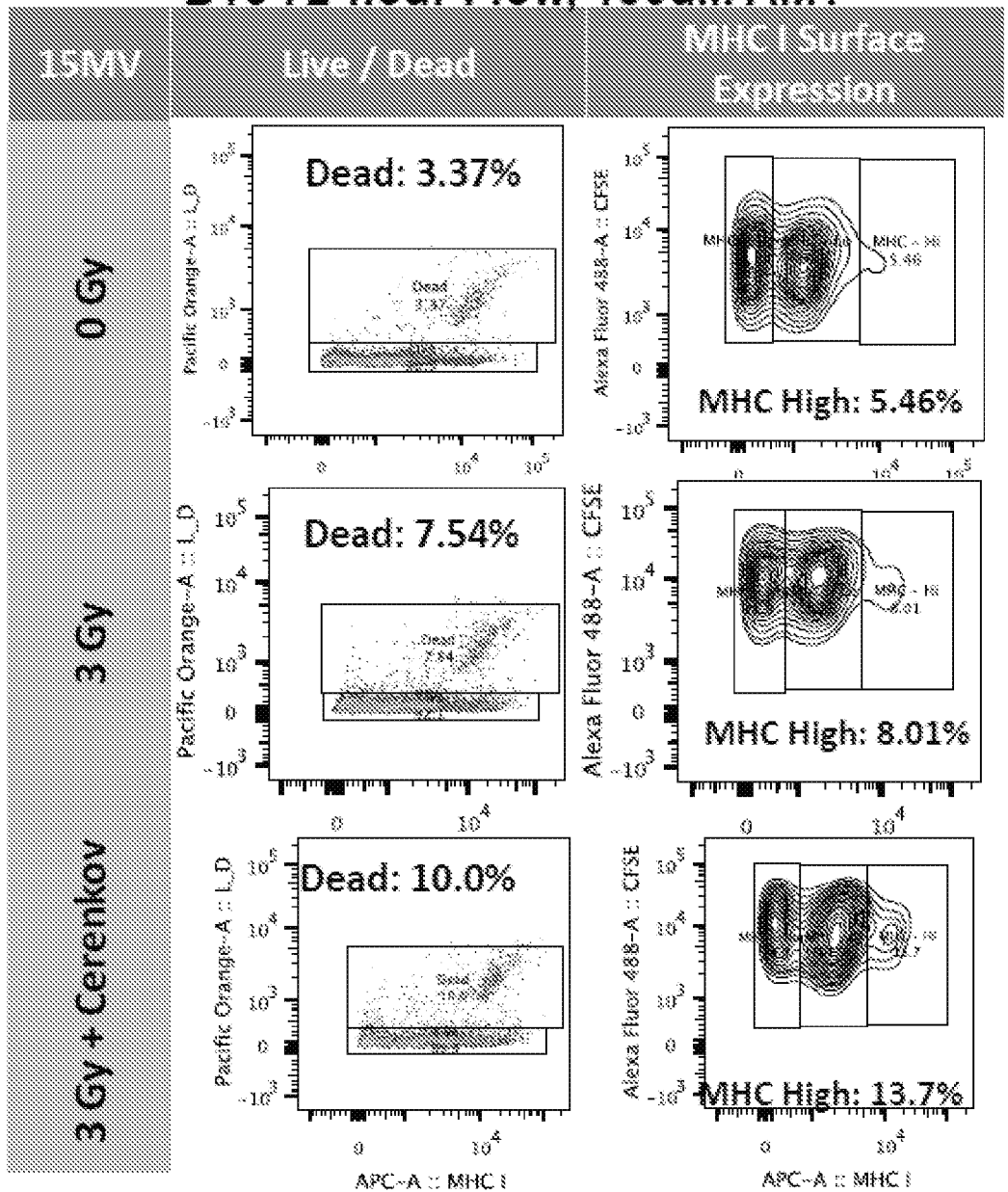
FIG. 7C is a plot of the results of FIG. 7B with the data presented in terms of cell kill and MHC fraction.

Prions that are treatable in the invention are proteins that can access multiple conformations, at least one of which is beta-sheet rich, infectious and self-perpetuating in nature. These infectious proteins show several remarkable biological activities, including the ability to form multiple infectious prion conformations, also known as strains or variants, encoding unique biological phenotypes, and to establish and overcome prion species (transmission) barriers. See, e.g., Tessier et al., Unraveling infectious structures, strain variants and species barriers for the yeast prion [PSI+], Nat. Struct. Mol. Biol. 2009 June; 16(6):598-605.

Cancers that can be treated by this invention include solid mammalian tumors as well as hematological malignancies. Solid mammalian tumors include cancers of the head and neck, lung, mesothelioma, mediastinum, esophagus, stomach, pancreas, hepatobiliary system, small intestine, colon, colorectal, rectum, anus, kidney, urethra, bladder, prostate, urethra, penis, testis, gynecological organs, ovaries, breast, endocrine system, skin central nervous system; sarcomas of the soft tissue and bone; and melanoma of cutaneous and intraocular origin. Hematological malignancies include childhood leukemia and lymphomas, Hodgkin's disease, lymphomas of lymphocytic and cutaneous origin, acute and chronic leukemia, plasma cell neoplasm and cancers associated with AIDS. In addition, a cancer at any stage of progression can be treated, such as primary, metastatic, and recurrent cancers. Both human and veterinary uses are contemplated.

Besides cancers, other disorders of the lymph nodes (such as for example viral and/or bacterial infections) can be treated by this invention. Accordingly, in one embodiment of the invention, there is provided a method for treating a subject with a virus or a bacterium which 1) provides within lymph nodes of the subject at least one photoactive or photoactivatable drug for treatment of the virus or the bacterium, and 2) applies initiation energy from at least one source to the lymph nodes. The method 3) activates by the CR light directly or indirectly the at least one photoactive or photoactivatable drug at the target inside the lymph nodes. Inside the lymph nodes, the method 4) reacts the activated drug with the virus or bacterium to inactivate the virus or the bacterium to thereby treat the subject.

Experimental Results

Experimental testing of the functioning of the low mass (or low atomic number) radiation filters of the present invention and (in general) of the capability of preferentially-produced Cherenkov radiation to change the viability of cells and/or to activate psoralen has been undertaken by the inventors.

FIG. 6A is a schematic of the experimental setup used to ascertain the relative Cherenkov radiation output (from different radiation filters) per x-ray dose (i.e., normalized to a standard x-ray flux). In FIG. 6A, a linear accelerator MV x-ray source produced a spectrum of high energy x-rays which were transmitted through various "test" low radiation filters of the present invention. The resultant x-ray flux was then transmitted into a phantom (i.e., a 17.8×17.8×17.8 $cm^3$ container of water with 0.5 g/L quinine sulfate booster). Inside the container, an ion chamber x-ray detector counted the x-rays, and an optical fiber collected UV-Vis Cherenkov light produced inside the quinine sulfate solution. The low atomic number or law mass radiation filters of the invention preferentially filter out low energy x-rays which deliver radiation dose but which result in little if any Cherenkov light.

FIG. 6B is a plot of the measured Cherenkov radiation output normalized to account for differences in the total x-ray dose having been transmitted into the quinine sulfate solution for the different filters: with no filter, with a 1 cm thick carbon filter, with a 2 cm thick carbon filter, and with a 10 cm thick polyurethane filter. The results in FIG. 6B show that these test filters were effective in providing an x-ray spectrum of x-ray fluxes that preferentially generate more Cherenkov radiation.

FIG. 6C is a comparison of the UV-Vis Cherenkov light spectrum showing that the light produced has the same or nearly the same spectrum when no filter was used and when the 10 cm thick polyurethane filter was used.

In order to show the efficacy of UV-Vis Cherenkov light in a biological medium, both x-ray flux from the above-noted linear accelerator and optionally UV-Vis Cherenkov light from the above-noted phantom were allowed to simultaneously expose proximate wells of B16 melanoma assay, with one cell receiving both x-rays and UV-Vis Cherenkov light and a proximate cell receiving only x-rays. Different concentrations of 4,5',8-trimethyl psoralen (TMP) are applied to different wells containing the B16 melanoma cells. The toxicity (cell kill) of the TMP in the different cells was measure to provide a baseline toxicity (no x-rays, no UV-Vis Cherenkov light).

FIG. 7A is a plot of cell kill as a function of TMP concentration with and without Cherenkov (i.e. with and without the UV-Vis Cherenkov light) after exposure to 6 MV x-rays at a 2 Gy dose. The cell kill was measured after a 48-hour incubation time. Specifically, a CellTiter-Glo™ luminescence (cell viability) measurement versus concentration of TMP was made with or without Cherenkov light. The CellTiter-Glo™ luminescence technique involves the introduction of MTT (3-(4,5-dimethylthiazol-2-yl)-2,5-diphenyltetrazolium bromide) into the wells containing the B16 melanoma cells. Viable cells with active metabolism convert MTT into a purple colored formazan product with an absorbance maximum near 570 nm. The amount of the purple colored formazan product is proportional to the number of living cells. Accordingly, the quantity of formazan (presumed directly proportional to the number of viable cells) is measured by recording changes in absorbance at 570 nm using a plate reading spectrophotometer.

The data in FIG. 7A of the invention utilizing the CellTiter-Glo™ luminescence technique shows that cell viability is reduced in those cells which received Cherenkov light, with the higher doses of TMP showing higher cell kill. These results show that more cancer cells were killed with than without Cherenkov light, suggesting activation of the TMP by the Cherenkov light, thus showing higher activity against the cancer cells.

FIG. 7B is a plot of the flow cytometry data acquired from B16 melanoma cells indicating a similar effect to the cytotoxicity depicted in FIG. 7A. With this technique, MHC class I molecules present peptides to cytotoxic cells. Only peptides with the right length and sequence bind to the nascent MHC class I molecules in the assay. Accordingly, when cytotoxic products from cell kill of the B16 melanoma cells are present, these products will be bound to surface containing the MHC class I molecules, which was then evaluated by flow cytometry. The data of FIG. 7B shows the results for a 15 MV X-ray exposure after a 72 hour incubation.

The data of FIG. 7C shows the results for the 15 MV X-ray exposure after the 72 hour incubation with the data presented in terms of cell kill. The relatively high MHC 1 expression (13.7% vs. 8.01% and 5.46% for the controls with no Cherenkov and with no x-rays) is consistent with an immunogenic response.

STATEMENTS OF THE INVENTION

The following statements of the invention express generalized aspects of the invention. While presented in a numeric format and in a sequential order, the aspects set forth in each of the statements are combinable in whole or in part to provide for the present inventions methods and systems set out below. The generalized aspects of the invention set forth in each of the statements are also combinable with elements of the invention described above and claimed below:

1. A method for treating a subject with a disorder, comprising:

providing within the subject at least one photoactivatable drug for treatment of the subject; applying initiation energy from at least one source to generate inside the subject a preferential x-ray flux for generation of Cherenkov radiation (CR) light capable of activating the at least one photoactivatable drug; and from said CR light, activating inside the subject the at least one photoactivatable drug to thereby treat the disorder. (The preferential x-ray flux in the medium of the subject produces more Cherenkov radiation per x-ray dose than its original x-ray spectrum from its original source would have produced in the subject.)

2. The method of statement 1, wherein applying comprises applying the initiation energy through a filter preferentially removing lower energy x-rays while transmitting higher energy x-rays.

3. The method of statements 1 or 2, wherein applying comprises applying the initiation energy through a low mass filter.

4. The method of statements 1, 2, or 3, wherein applying the initiation energy through a low mass filter comprises applying the initiation energy through a section of carbon-containing material which is between 1 cm and 20 cm thick.

5. The method of statements 1, 2, or 3, wherein applying the initiation energy through a low mass filter comprises applying the initiation energy through a section of carbon-containing material which is between 5 cm and 15 cm thick.

6. The method of statements 1, 2, or 3, wherein applying the initiation energy through a low mass filter comprises applying the initiation energy through a section of carbon-containing material which is between 7 cm and 12 cm thick.

7. The method of statements 1, 2, or 3, wherein applying the initiation energy through a low mass filter comprises applying the initiation energy through a section of carbon-containing material containing at least one of H, F, Si, N, P, and B.

8. The method of statements 1, 2, or 3, wherein applying the initiation energy through a low mass filter comprises applying the initiation energy through a section of carbon-containing material containing in a minority amount at least one of H, F, Si, N, P, and B.

9. The method of any one or more of the statements above, wherein activating inside the subject the at least one photoactivatable drug comprises bonding the photoactivatable drug to a cellular structure.

10. The method of statement 9, wherein the bonding comprises at least one of 1) bonding the photoactivatable drug to at least one of nuclear DNA, mRNA, rRNA, ribosome, mitochondrial DNA and 2) bonding the photoactivatable drug to lipid bilayers of a virus.

11. The method of statement 9, wherein the bonding comprises bonding the photoactivatable drug to lipid bilayers of at least one virus selected from the group consisting of an ebola virus, an encephalitis virus, a West Nile virus, and an HIV virus.

12. The method of any one or more of the statements above, further comprising activating inside the subject the at least one photoactivatable drug comprises activating a psoralen.

13. The method of any one or more of the statements above, further comprising activating inside the subject the at least one photoactivatable drug comprises activating 8 MOP or AMT.

14. The method of any one or more of the statements above, wherein activating inside the subject the at least one photoactivatable drug comprises activating an alkylating agent.

15. The method of any one or more of the statements above, wherein activating inside the subject the at least one photoactivatable drug comprises activating 1,5-iodonophthylazide.

16. The method of any one or more of the statements above, wherein activating inside the subject the at least one photoactivatable drug comprises activating a drug for treating the cell proliferation disorders.

17. The method of any one or more of the statements above, wherein activating inside the subject the at least one photoactivatable drug comprises activating a drug for treating at least one of a virus or a bacterium.

18. The method of any one or more of the statements above, further comprising energy modulating the CR light with a fluorophore.

19. The method of any one or more of the statements above, further comprising activating a biological response inside the subject.

20. The method of any one or more of the statements above, wherein applying initiation energy comprises applying a filtered set of x-rays to the subject having an energy of at least 0.5 MeV and less than 10 MeV.

21. The method of any one or more of the statements above, wherein applying initiation energy comprises applying a filtered set of x-rays to the subject having an energy of at least 1.0 MeV and less than 10 MeV.

22. The method of any one or more of the statements above, wherein applying initiation energy comprises applying a filtered set of x-rays to the subject having an energy of at least 1.5 MeV and less than 10 MeV.

23. The method of any one or more of the statements above, wherein applying initiation energy comprises applying a filtered set of x-rays to the subject having an energy of at least 1.0 MeV and less than 10 MeV.

24. The method of any one or more of the statements above, wherein activating inside the subject the at least one photoactivatable drug comprises activating at least one of photoactivating a drug, sterilizing the target structure, photoactivating a psoralen, photoactivating iodonophthylazide, generating a reactive oxygen speciesor a combination thereof.

25. The method of any one or more of the statements above, wherein activating inside the subject the at least one photoactivatable drug comprises inducing an autoimmune response, exciting a DNA strand of a cancer cell, redirecting a metabolic pathway, up-regulating genes, down-regulating genes, secreting cytokines, altering cytokine receptor responses, releasing metabolites, generating a vaccine, or a combination thereof.

26. The method of any one or more of the statements above, wherein activating inside the subject the at least one photoactivatable drug comprises altering a cellular response or a metabolic rate of the target structure.

27. The method of any one or more of the statements above, further comprising administering at least one energy modulation agent which adsorbs, intensifies or modifies said CR light.

28. The method of statement 27, wherein said energy modulation agent comprises at least one of a biocompatible fluorescing metal nanoparticle, fluorescing metal oxide nanoparticle, fluorescing metal coated metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a fluorophore, a fluorescent material, a phosphorescent material, a biocompatible phosphorescent molecule, and a lanthanide chelate.

29. The method of statement 27, wherein said energy modulation agent comprises a down-converting agent.

30. The method of statement 29, wherein said energy modulation agent comprises inorganic materials selected from the group consisting of: metal oxides; metal sulfides; doped metal oxides; and mixed metal chalcogenides.

31. The method of statement 29, wherein said energy modulation agent comprises at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, ZnS; ZnSe; MgS; CaS, $CaWO_4$, $CaSiO_2$:Pb, and alkali lead silicate including compositions of $SiO_2$, $B_2O_3$, $Na_2O$, $K_2O$, PbO, MgO, or Ag, and combinations or alloys or layers thereof.

32. The method of statement 29, wherein said energy modulation agent comprises at least one of ZnSeS:Cu, Ag, Ce, Tb; CaS: Ce,Sm; $La_2O_2S$:Tb; $Y_2O_2S$:Tb; $Gd_2O_2S$:Pr, Ce, F; $LaPO_4$.

33. The method of statement 29, wherein said energy modulation agent comprises at least one of ZnS:Ag, ZnS:Cu, Pb, and alloys of the ZnSeS.

34. The method of statement 29, wherein said energy modulation agent comprises at least one of sodium yttrium fluoride ($NaYF_4$), lanthanum fluoride ($LaF_3$), lanthanum oxysulfide ($La_2O_2S$), yttrium oxysulfide ($Y_2O_2S$), yttrium fluoride ($YF_3$), yttrium gallate, yttrium aluminum garnet (YAG), gadolinium fluoride ($GdF_3$), barium yttrium fluoride ($BaYF_5$, $BaY_2F_8$), gadolinium oxysulfide ($Gd_2O_2S$), calcium tungstate ($CaWO_4$), yttrium oxide:terbium ($Yt_2O_3$Tb), gadolinium oxysulphide:europium ($Gd_2O_2S$:Eu), lanthanum oxysulphide:europium ($La_2O_2S$:Eu), and gadolinium oxysulphide:promethium, cerium, fluorine ($Gd_2O_2S$:Pr,Ce, F), $YPO_4$:Nd, $LaPO_4$:Pr, $(Ca,Mg)SO_4$:Pb, $YBO_3$:Pr, $Y_2SiO_5$:Pr, $Y_2Si_2O_7$:Pr, $SrLi_2SiO_4$:Pr,Na, and $CaLi_2SiO_4$:Pr.

35. The method of statement 29, wherein said energy modulation agent comprises at least one of $KSrPO_4$:$Eu^{2+}$, $Pr^{3+}$, $NaGdF_4$:Eu, $Zn_2SiO_4$:$Tb^{3+}$,$Yb^{3+}$, β-$NaGdF_4$ co-doped with $Ce^{3+}$ and $Tb^{3+}$ ions, and $Gd_2O_2S$:Tm or $BaYFs$:$Eu^{3+}$.

36. The method of statement 27, wherein said energy modulation agent comprises an up converting agent.

37. The method of statement 36, wherein said energy modulation agent at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

38. The method of any one or more of the statements above, further comprising providing a plasmonics-active agent which enhances or modifies the CR light.

39. The method of statement 38, wherein the plasmonics-active agent comprises metal nanostructures.

40. The method of statement 39, wherein the metal nanostructures are nanospheres, nanorods, nanocubes, nanopyramids, nanoshells, multi-layer nanoshells and combinations thereof.

41. The method of any one or more of the statements above, wherein the initiation energy comprises at least one or more of x-rays, gamma rays, an electron beam, or a proton beam.

42. The method of any one or more of the statements above, further comprising treating with said Cherenkov radiation at least one condition selected from the group consisting of cancer, bacterial infection, parasitic infection, prion infection, fungal infection, immune rejection response, autoimmune disorder, and aplastic condition.

43. The method of any one or more of the statements above, further comprising treating with said Cherenkov radiation a condition, a disorder, or a disease selected from the group consisting of cardiac ablasion, photoangioplastic condition, intimal hyperplasia, arteriovenous fistula, macular degeneration, psoriasis, acne, hopecia areata, portwine spots, hair removal, autoimmune diseases, rheumatoid and inflammatory arthritis, behavioral and cognitive disorder/condition, joint condition, Parkinson's disease, retinal injury and other ocular diseases, enlarged prostate, varicose veins, reduction or removal of fat deposits (liposuction), nerve regeneration, sensory regeneration/restoration, wound healing, chronic pain, conditions occurring in bone tissue, conditions occurring in a soft tissue and/or cartilage, and lymph node condition.

44. The method of any one or more of the statements above, wherein the at least one photoactivatable drug comprise at least one pharmaceutical agent selected from the group consisting of a psoralen, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolite, vitamin precursor, naphthoquinone, naphthalene, naphthol and derivatives thereof having planar molecular conformations, porphorinporphyrin, dye and phenothiazine derivative, coumarin, quinolone, quinone, and anthroquinone.

45. The method of any one or more of the statements above, wherein the at least one photoactivatable drug comprises one or more of a psoralen, a coumarin, a porphyrin, and iodonophthylazide, or a derivative thereof.

46. The method of any one or more of the statements above, wherein the at least one photoactivatable drug comprises at least one pharmaceutical agent selected from the group consisting of 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematophorphyrin, and phthadocyanine.

47. The method of any one or more of the statements above, wherein the at least one photoactivatable drug comprises an alkylating agent and psoralen.

48. A system for treating a subject with a disorder, comprising:
a drug administrator which provides within the subject at least one photoactivatable drug for treatment of the subject, an initiation energy source which provides inside the subject a preferential x-ray flux for generation of Cherenkov radiation (CR) light capable of activating at least one photoactivatable drug, wherein the CR light activates inside the subject the at least one photoactivatable drug to thereby treat the disorder.

49. The system of statement 48, further comprising a processor which controls any of the steps set forth in statements 1-47.

50. The system of statement 48, further comprising a filter which preferentially removes lower energy x-rays while transmitting higher energy x-rays.

51. The system of statement 50, wherein the filter comprises a low mass filter.

52. The system of statement 50, wherein the low mass filter comprises a section of carbon-containing material which is between 1 cm and 20 cm thick.

53. The system of statement 50, wherein the low mass filter comprises a section of carbon-containing material which is between 5 cm and 15 cm thick.

54. The system of statement 50, wherein the low mass filter comprises a section of carbon-containing material which is between 7 cm and 12 cm thick.

55. The system of statement 50, wherein the low mass filter comprises a section of carbon-containing material containing at least one of H, F, Si, N, P, and B.

56. The system of statement 50, wherein the low mass filter comprises a section of carbon-containing material containing in a minority amount at least one of H, F, Si, N, P, and B.

Numerous modifications and variations of the present invention are possible in light of the above teachings. It is therefore to be understood that within the scope of the appended claims, the invention may be practiced otherwise than as specifically described herein.

The invention claimed is:

1. A method for treating a subject with a disorder, comprising:
providing within the subject at least one photoactivatable drug for treatment of the subject;
applying initiation energy from at least one source to generate inside the subject a preferential x-ray flux for generation of Cherenkov radiation (CR) light capable of activating the at least one photoactivatable drug, wherein the initiation energy is applied through a filter preferentially removing lower energy x-rays while transmitting higher energy x-rays; and
from said CR light, activating inside the subject the at least one photoactivatable drug to thereby treat the disorder.

2. The method of claim 1, wherein applying comprises applying the initiation energy through a low mass filter.

3. The method of claim 2, wherein applying the initiation energy through a low mass filter comprises applying the initiation energy through a section of carbon-containing material which is between 1 cm and 20 cm thick.

4. The method of claim 2, wherein applying the initiation energy through a low mass filter comprises applying the initiation energy through a section of carbon-containing material which is between 5 cm and 15 cm thick.

5. The method of claim 2, wherein applying the initiation energy through a low mass filter comprises applying the initiation energy through a section of carbon-containing material which is between 7 cm and 12 cm thick.

6. The method of claim 2, wherein applying the initiation energy through a low mass filter comprises applying the initiation energy through a section of carbon-containing material containing at least one of H, F, Si, N, P, and B.

7. The method of claim 2, wherein applying the initiation energy through a low mass filter comprises applying the initiation energy through a section of carbon-containing material containing in a minority amount at least one of H, F, Si, N, P, and B.

8. The method of claim 1, wherein activating inside the subject the at least one photoactivatable drug comprises bonding the photoactivatable drug to a cellular structure.

9. The method of claim 8, wherein the bonding comprises at least one of 1) bonding the photoactivatable drug to at least one of nuclear DNA, mRNA, rRNA, ribosome, mitochondrial DNA and 2) bonding the photoactivatable drug to lipid bilayers of a virus.

10. The method of claim 8, wherein the bonding comprises bonding the photoactivatable drug to lipid bilayers of at least one virus selected from the group consisting of an ebola virus, an encephalitis virus, a West Nile virus, and an HIV virus.

11. The method of claim 1, further comprising activating inside the subject the at least one photoactivatable drug comprises activating a psoralen.

12. The method of claim 1, further comprising activating inside the subject the at least one photoactivatable drug comprises activating 8 MOP or AMT.

13. The method of claim 1, wherein activating inside the subject the at least one photoactivatable drug comprises activating an alkylating agent.

14. The method of claim 1, wherein activating inside the subject the at least one photoactivatable drug comprises activating 1,5-iodonophthylazide.

15. The method of claim 1, wherein activating inside the subject the at least one photoactivatable drug comprises activating a drug for treating a cell proliferation disorder.

16. The method of claim 1, wherein activating inside the subject the at least one photoactivatable drug comprises activating a drug for treating at least one of a virus or a bacterium.

17. The method of claim 1, further comprising energy modulating the CR light with a fluorophore.

18. The method of claim 17, further comprising activating a biological response inside the subject.

19. The method of claim 1, wherein applying initiation energy comprises applying a filtered set of x-rays to the subject having an energy of at least 0.5 MeV and less than 10 MeV.

20. The method of claim 1, wherein applying initiation energy comprises applying a filtered set of x-rays to the subject having an energy of at least 1.0 MeV and less than 10 MeV.

21. The method of claim 1, wherein applying initiation energy comprises applying a filtered set of x-rays to the subject having an energy of at least 1.5 MeV and less than 10 MeV.

22. The method of claim 1, wherein applying initiation energy comprises applying a filtered set of x-rays to the subject having an energy of at least 1.0 MeV and less than 10 MeV.

23. The method of claim 1, wherein activating inside the subject the at least one photoactivatable drug comprises activating at least one of photoactivating a drug, sterilizing the target structure, photoactivating a psoralen, photoactivating iodonophthylazide, generating a reactive oxygen species or a combination thereof.

24. The method of claim 1, wherein activating inside the subject the at least one photoactivatable drug comprises inducing an autoimmune response, exciting a DNA strand of a cancer cell, redirecting a metabolic pathway, up-regulating genes, down-regulating genes, secreting cytokines, altering cytokine receptor responses, releasing metabolites, generating a vaccine, or a combination thereof.

25. The method of claim 1, wherein activating inside the subject the at least one photoactivatable drug comprises altering a cellular response or a metabolic rate of the target structure.

26. The method of claim 1, further comprising administering at least one energy modulation agent which adsorbs, intensifies or modifies said CR light.

27. The method of claim 26, wherein said energy modulation agent comprises at least one of a biocompatible fluorescing metal nanoparticle, fluorescing metal oxide nanoparticle, fluorescing metal coated metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a fluorophore, a fluorescent material, a phosphorescent material, a biocompatible phosphorescent molecule, and a lanthanide chelate.

28. The method of claim 26, wherein said energy modulation agent comprises a down-converting agent.

29. The method of claim 28, wherein said energy modulation agent comprises inorganic materials selected from the group consisting of: metal oxides; metal sulfides; doped metal oxides; and mixed metal chalcogenides.

30. The method of claim 28, wherein said energy modulation agent comprises at least one of $Y_2O_3$, $Y_2O_2S$, $NaYF_4$, $NaYbF_4$, YAG, YAP, $Nd_2O_3$, $LaF_3$, $LaC1_3$, $La_2O_3$, $TiO_2$, $LuPO_4$, $YVO_4$, $YbF_3$, $YF_3$, Na-doped $YbF_3$, ZnS; ZnSe; MgS; CaS, $CaWO_4$, $CaSiO_2$:Pb, and alkali lead silicate including compositions of $SiO_2$, $B_2O_3$, $Na_2O$, $1(_20$, PbO, MgO, or Ag, and combinations or alloys or layers thereof.

31. The method of claim 28, wherein said energy modulation agent comprises at least one of ZnSeS:Cu, Ag, Ce, Tb; CaS: Ce,Sm; $La_2O_2S$:Tb; $Y_2O_2S$:Tb;
$Gd_2O_2S$:Pr, Ce, F; $LaPO_4$.

32. The method of claim 28, wherein said energy modulation agent comprises at least one of ZnS:Ag, ZnS:Cu, Pb, and alloys of the ZnSeS.

33. The method of claim 28, wherein said energy modulation agent comprises at least one of sodium yttrium fluoride ($NaYF_4$), lanthanum fluoride ($LaF_3$), lanthanum oxysulfide ($La_2O_2S$), yttrium oxysulfide ($Y_2O_2S$), yttrium fluoride ($YF_3$), yttrium gallate, yttrium aluminum garnet (YAG), gadolinium fluoride ($GdF_3$), barium yttrium fluoride ($BaYF_5$, $BaY_2F_8$), gadolinium oxysulfide ($Gd_2O_2S$), calcium tungstate ($CaWO_4$), yttrium oxide:terbium ($Yt_2O_3Tb$), gadolinium oxysulphide:europium ($Gd_2O_2S$:Eu), lanthanum oxysulphide:europium ($La_2O_2S$:Eu), and gadolinium oxysulphide:promethium, cerium, fluorine ($Gd_2O_2S$:Pr,Ce, F), $YPO_4$:Nd, $LaPO_4$:Pr, $(Ca,Mg)SO_4$:Pb, $YBO_3$:Pr, $Y_2SiO_5$:Pr, $Y_2Si_2O_7$:Pr, $SrLi_2SiO_4$:Pr,Na, and $CaLi_2SiO_4$: Pr.

34. The method of claim 28, wherein said energy modulation agent comprises at least one of $KSrPO_4$:$Eu^{2+}$, $Pr^{3+}$, $NaGdF_4$:Eu, $Zn_2SiO_4$:$Tb^{3+}$, $Yb^{3+,}$ $^{\beta\text{-}NaGdF}4$ co-doped with $Ce^{3+}$and $Tb^{3+}$ions, and $Gd_2O_2S$:Tm or $BaYF_5$:$Eu^{3+}$.

35. The method of claim 26, wherein said energy modulation agent comprises an up converting agent.

36. The method of claim 35, wherein said energy modulation agent at least one of $Y_2O_3$, $Y_2O_2S$, $NaYF_4$, $NaYbF_4$, YAG, YAP, $Nd_2O_3$, $LaF_3$, $LaC1_3$, $La_2O_3$, $TiO_2$, $LuPO_4$, $YVO_4$, $YbF_3$, $YF_3$, Na-doped $YbF_3$, or $SiO_2$ or alloys or layers thereof.

37. The method of claim 1, further comprising providing a plasmonics-active agent which enhances or modifies the CR light.

38. The method of claim 37, wherein the plasmonics-active agent comprises metal nanostructures.

39. The method of claim 38, wherein the metal nanostructures are nanospheres, nanorods, nanocubes, nanopyramids, nanoshells, multi-layer nanoshells and combinations thereof.

40. The method of claim 1, wherein the initiation energy comprises at least one or more of x-rays, gamma rays, an electron beam, or a proton beam.

41. The method of claim 1, further comprising treating with said Cherenkov radiation at least one condition selected from the group consisting of cancer, bacterial infection, parasitic infection, prion infection, fungal infection, immune rejection response, autoimmune disorder, and aplastic condition.

42. The method of claim 1, further comprising treating with said Cherenkov radiation a condition, a disorder, or a disease selected from the group consisting of cardiac ablation, photoangioplastic condition, intimal hyperplasia, arteriovenous fistula, macular degeneration, psoriasis, acne, hopecia areata, portwine spots, hair removal, autoimmune diseases, rheumatoid and inflammatory arthritis, behavioral and cognitive disorder/condition, joint condition, Parkinson's disease, retinal injury and other ocular diseases, enlarged prostate, varicose veins, reduction or removal of fat deposits (liposuction), nerve regeneration, sensory regeneration/restoration, wound healing, chronic pain, conditions occurring in bone tissue, conditions occurring in a soft tissue and/or cartilage, and lymph node condition.

43. The method of claim 1, wherein the at least one photoactivatable drug comprise at least one pharmaceutical agent selected from the group consisting of a psoralen, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolite, vitamin precursor, naphthoquinone, naphthalene, naphthol and derivatives thereof having planar molecular conformations, porphorin-porphyrin, dye and phenothiazine derivative, coumarin, quinolone, quinone, and anthroquinone.

44. The method of claim 1, wherein the at least one photoactivatable drug comprises one or more of a psoralen, a coumarin, a porphyrin, and iodonophthylazide, or a derivative thereof.

45. The method of claim 1, wherein the at least one photoactivatable drug comprises at least one pharmaceutical agent selected from the group consisting of 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematophorphyrin, and phthadocyanine.

46. The method of claim 1, wherein the at least one photoactivatable drug comprises an alkylating agent and psoralen.

47. A system for treating a subject with a disorder, comprising:
a drug administration device which provides within the subject at least one photoactivatable drug for treatment of the subject,
an initiation energy source which provides inside the subject a preferential x-ray flux for generation of Cherenkov radiation (CR) light capable of activating at least one photoactivatable drug, and a filter which preferentially removes lower energy x-rays from said preferential x-ray flux while transmitting higher energy x-rays from said preferential x-ray flux;
wherein the CR light activates inside the subject the at least one photoactivatable drug to thereby treat the disorder.

48. The system of claim 47, wherein the filter comprises a low mass filter.

49. The system of claim 47, wherein the low mass filter comprises a section of carbon-containing material which is between 1 cm and 20 cm thick.

50. The system of claim 47, wherein the low mass filter comprises a section of carbon-containing material which is between 5 cm and 15 cm thick.

51. The system of claim 47, wherein the low mass filter comprises a section of carbon-containing material which is between 7 cm and 12 cm thick.

52. The system of claim 47, wherein the low mass filter comprises a section of carbon-containing material containing at least one of H, F, Si, N, P, and B.

53. The system of claim 47, wherein the low mass filter comprises a section of carbon-containing material containing in a minority amount at least one of H, F, Si, N, P, and B.

54. A method for treating a subject with a disorder, comprising:
providing within the subject at least one photoactivatable drug for treatment of the subject;
applying initiation energy from at least one source to generate inside the subject a preferential x-ray flux for generation of Cherenkov radiation (CR) light capable of activating the at least one photoactivatable drug; and
from said CR light, activating inside the subject the at least one photoactivatable drug to thereby treat the disorder, wherein activating inside the subject the at least one photoactivatable drug comprises activating a drug for treating a cell proliferation disorder, a virus or a bacterium.

55. The method of claim 54, wherein applying comprises applying the initiation energy through a filter preferentially removing lower energy x-rays while transmitting higher energy x-rays.

56. The method of claim 54, wherein applying comprises applying the initiation energy through a low mass filter.

57. The method of claim 56, wherein applying the initiation energy through a low mass filter comprises applying the initiation energy through a section of carbon-containing material which is between 1 cm and 20 cm thick.

58. The method of claim 56, wherein applying the initiation energy through a low mass filter comprises applying the initiation energy through a section of carbon-containing material which is between 5 cm and 15 cm thick.

59. The method of claim 56, wherein applying the initiation energy through a low mass filter comprises applying the initiation energy through a section of carbon-containing material which is between 7 cm and 12 cm thick.

60. The method of claim 56, wherein applying the initiation energy through a low mass filter comprises applying the initiation energy through a section of carbon-containing material containing at least one of H, F, Si, N, P, and B.

61. The method of claim 56, wherein applying the initiation energy through a low mass filter comprises applying the initiation energy through a section of carbon-containing material containing in a minority amount at least one of H, F, Si, N, P, and B.

62. The method of claim 54, wherein activating inside the subject the at least one photoactivatable drug comprises bonding the photoactivatable drug to a cellular structure.

63. The method of claim 62, wherein the bonding comprises at least one of 1) bonding the photoactivatable drug to at least one of nuclear DNA, mRNA, rRNA, ribosome, mitochondrial DNA and 2) bonding the photoactivatable drug to lipid bilayers of a virus.

64. The method of claim 62, wherein the bonding comprises bonding the photoactivatable drug to lipid bilayers of at least one virus selected from the group consisting of an ebola virus, an encephalitis virus, a West Nile virus, and an HIV virus.

65. The method of claim 54, further comprising activating inside the subject the at least one photoactivatable drug comprises activating a psoralen.

66. The method of claim 54, further comprising activating inside the subject the at least one photoactivatable drug comprises activating 8 MOP or AMT.

67. The method of claim 54, wherein activating inside the subject the at least one photoactivatable drug comprises activating an alkylating agent.

68. The method of claim 54, wherein activating inside the subject the at least one photoactivatable drug comprises activating 1,5-iodonophthylazide.

69. The method of claim 54, wherein activating inside the subject the at least one photoactivatable drug comprises activating the drug for treating the cell proliferation disorder.

70. The method of claim 54, wherein activating inside the subject the at least one photoactivatable drug comprises activating the drug for treating at least one of a virus or a bacterium.

71. The method of claim 54, further comprising energy modulating the CR light with a fluorophore.

72. The method of claim 71, further comprising activating a biological response inside the subject.

73. The method of claim 54, wherein applying initiation energy comprises applying a filtered set of x-rays to the subject having an energy of at least 0.5 MeV and less than 10 MeV.

74. The method of claim 54, wherein applying initiation energy comprises applying a filtered set of x-rays to the subject having an energy of at least 1.0 MeV and less than 10 MeV.

75. The method of claim 54, wherein applying initiation energy comprises applying a filtered set of x-rays to the subject having an energy of at least 1.5 MeV and less than 10 MeV.

76. The method of claim 54, wherein applying initiation energy comprises applying a filtered set of x-rays to the subject having an energy of at least 1.0 MeV and less than 10 MeV.

77. The method of claim 54, wherein activating inside the subject the at least one photoactivatable drug comprises activating at least one of photoactivating a drug, sterilizing the target structure, photoactivating a psoralen, photoactivating iodonophthylazide, generating a reactive oxygen speciesor a combination thereof.

78. The method of claim 54, wherein activating inside the subject the at least one photoactivatable drug comprises inducing an autoimmune response, exciting a DNA strand of a cancer cell, redirecting a metabolic pathway, up-regulating genes, down-regulating genes, secreting cytokines, altering cytokine receptor responses, releasing metabolites, generating a vaccine, or a combination thereof.

79. The method of claim 54, wherein activating inside the subject the at least one photoactivatable drug comprises altering a cellular response or a metabolic rate of the target structure.

80. The method of claim 54, further comprising administering at least one energy modulation agent which adsorbs, intensifies or modifies said CR light.

81. The method of claim 80, wherein said energy modulation agent comprises at least one of a biocompatible fluorescing metal nanoparticle, fluorescing metal oxide nanoparticle, fluorescing metal coated metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a fluorophore, a fluorescent material, a phosphorescent material, a biocompatible phosphorescent molecule, and a lanthanide chelate.

82. The method of claim 80, wherein said energy modulation agent comprises a down-converting agent.

83. The method of claim 82, wherein said energy modulation agent comprises inorganic materials selected from the group consisting of: metal oxides; metal sulfides; doped metal oxides; and mixed metal chalcogenides.

84. The method of claim 82, wherein said energy modulation agent comprises at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, ZnS; ZnSe; MgS; CaS, $CaWO_4$, $CaSiO_2$:Pb, and alkali lead silicate including compositions of $SiO_2$, $B_2O_3$, $Na_2O$, $1(_20$, Pb0, MgO, or Ag, and combinations or alloys or layers thereof.

85. The method of claim 82, wherein said energy modulation agent comprises at least one of ZnSeS:Cu, Ag, Ce, Tb; CaS: Ce,Sm; $La_2O_2S$:Tb; $Y_2O_2S$:Tb;
$Gd_2O_2S$:Pr, Ce, F; $LaPO_4$.

86. The method of claim 82, wherein said energy modulation agent comprises at least one of ZnS:Ag, ZnS:Cu, Pb, and alloys of the ZnSeS.

87. The method of claim 82, wherein said energy modulation agent comprises at least one of sodium yttrium fluoride ($NaYF_4$), lanthanum fluoride ($LaF_3$), lanthanum oxysulfide ($La_2O_2S$), yttrium oxysulfide ($Y_2O_2S$), yttrium fluoride ($YF_3$), yttrium gallate, yttrium aluminum garnet (YAG), gadolinium fluoride ($GdF_3$), barium yttrium fluoride ($BaYF_5$, $BaY_2F_8$), gadolinium oxysulfide ($Gd_2O_2S$), calcium tungstate ($CaWO_4$), yttrium oxide:terbium ($Yt_2O_3$Tb), gadolinium oxysulphide:europium ($Gd_2O_2S$:Eu), lanthanum oxysulphide:europium ($La_2O_2S$:Eu), and gadolinium oxysulphide:promethium, cerium, fluorine ($Gd_2O_2S$:Pr,Ce, F), $YPO_4$:Nd, $LaPO_4$:Pr, $(Ca,Mg)SO_4$:Pb, $YBO_3$:Pr, $Y_2SiO_5$:Pr, $Y_2Si_2O_7$:Pr, $SrLi_2SiO_4$:Pr,Na, and $CaLi_2SiO_4$: Pr.

88. The method of claim 82, wherein said energy modulation agent comprises at least one of $KSrPO_4$:$Eu^{2+}$, $Pr^{3+}$, $NaGdF_4$:Eu, $Zn_2SiO_4$:$Tb^{3+}$, $Yb^{3+}$, β-$NaGdF_4$ co-doped with $Ce^{3+}$ and $Tb^{3+}$ ions, and $Gd_2O_2S$:Tm or $BaYF_5$:$Eu^{3+}$.

89. The method of claim 82, wherein said energy modulation agent comprises an up converting agent.

90. The method of claim 89, wherein said energy modulation agent at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

91. The method of claim 54, further comprising providing a plasmonics-active agent which enhances or modifies the CR light.

92. The method of claim 91, wherein the plasmonics-active agent comprises metal nanostructures.

93. The method of claim 92, wherein the metal nanostructures are nanospheres, nanorods, nanocubes, nanopyramids, nanoshells, multi-layer nanoshells and combinations thereof.

94. The method of claim 54, wherein the initiation energy comprises at least one or more of x-rays, gamma rays, an electron beam, or a proton beam.

95. The method of claim 54, further comprising treating with said Cherenkov radiation at least one condition selected from the group consisting of cancer, bacterial infection, parasitic infection, prion infection, fungal infection, immune rejection response, autoimmune disorder, and aplastic condition.

96. The method of claim 1, further comprising treating with said Cherenkov radiation a condition, a disorder, or a disease selected from the group consisting of cardiac ablation, photoangioplastic condition, intimal hyperplasia, arteriovenous fistula, macular degeneration, psoriasis, acne, hopecia areata, portwine spots, hair removal, autoimmune diseases, rheumatoid and inflammatory arthritis, behavioral and cognitive disorder/condition, joint condition, Parkinson's disease, retinal injury and other ocular diseases, enlarged prostate, varicose veins, reduction or removal of fat deposits (liposuction), nerve regeneration, sensory regeneration/restoration, wound healing, chronic pain, conditions occurring in bone tissue, conditions occurring in a soft tissue and/or cartilage, and lymph node condition.

97. The method of claim 54, wherein the at least one photoactivatable drug comprise at least one pharmaceutical agent selected from the group consisting of a psoralen, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolite, vitamin precursor, naphthoquinone, naphthalene, naphthol and derivatives thereof having planar molecular conformations, porphorinporphyrin, dye and phenothiazine derivative, coumarin, quinolone, quinone, and anthroquinone.

98. The method of claim 54, wherein the at least one photoactivatable drug comprises one or more of a psoralen, a coumarin, a porphyrin, and iodonophthylazide, or a derivative thereof.

99. The method of claim 54, wherein the at least one photoactivatable drug comprises at least one pharmaceutical agent selected from the group consisting of 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematophorphyrin, and phthadocyanine.

100. The method of claim 54, wherein the at least one photoactivatable drug comprises an alkylating agent and psoralen.

\* \* \* \* \*

UNITED STATES PATENT AND TRADEMARK OFFICE
CERTIFICATE OF CORRECTION

PATENT NO. : 11,135,294 B2
APPLICATION NO. : 15/770926
DATED : October 5, 2021
INVENTOR(S) : Oldham et al.

It is certified that error appears in the above-identified patent and that said Letters Patent is hereby corrected as shown below:

In the Specification

In Column 4, Line 7, delete "a" and insert -- an --, therefor.

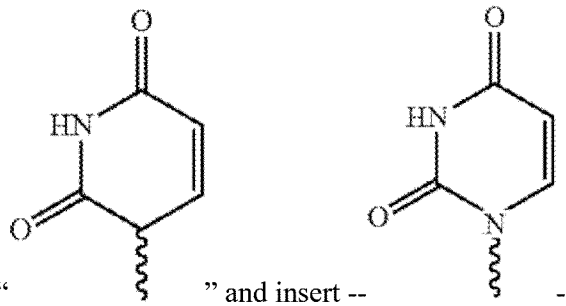

In Column 4, Lines 17-23, delete " " and insert -- --, therefor.

In Column 6, Lines 41-42, delete "sinbis virus, cytomegaloviris," and insert -- sindbis virus, cytomegalovirus, --, therefor.

In Column 14, Line 62, delete "Tomograph" and insert -- Tomography --, therefor.

In Column 16, Line 56, delete "mitochondriat" and insert -- mitochondria --, therefor.

In Column 17, Line 64, delete "downconverion" and insert -- downconversion --, therefor.

In Column 23, Line 9, delete "This" and insert -- this --, therefor.

In Column 27, Line 34, delete "ablasion" and insert -- ablation --, therefor.

In Column 27, Line 35, delete "arrhythmiand" and insert -- arrhythmia and --, therefor.

In Column 27, Line 38, delete "hopeciareata," and insert -- alopecia areata, --, therefor.

Signed and Sealed this
Eleventh Day of October, 2022

*Katherine Kelly Vidal*
Katherine Kelly Vidal
*Director of the United States Patent and Trademark Office*

CERTIFICATE OF CORRECTION (continued)
U.S. Pat. No. 11,135,294 B2

In Column 44, Line 61, delete "speciesor" and insert -- species or --, therefor.

In Column 46, Line 24, delete "ablasion," and insert -- ablation, --, therefor.

In Column 46, Line 26, delete "hopecia" and insert -- alopecia --, therefor.

In Column 46, Lines 59-60, delete "tetrasulonate, hematophorphyrin, and phthadocyanine." and insert -- tetrasulfonate, hematoporphyrin, and phthalocyanine. --, therefor.

In the Claims

In Column 49, Claim 30, Line 31, delete "LaC$^1$$_3$," and insert -- LaCl$_3$, --, therefor.

In Column 49, Claim 30, Line 34, delete "1($_2$0," and insert -- K$_2$O, --, therefor.

In Column 49, Claim 34, Line 59, delete "$^{\beta\text{-NaGdF}}$$_4$" and insert -- β-NaGdF$_4$ --, therefor.

In Column 49, Claim 36, Line 65, delete "LaCl$_3$," and insert -- LaCl$_3$, --, therefor.

In Column 50, Claim 42, Lines 21-22, delete "ablasion," and insert -- ablation, --, therefor.

In Column 50, Claim 42, Line 24, delete "hopecia" and insert -- alopecia --, therefor.

In Column 50, Claim 45, Line 55, delete "tetrasulonate, hematophorphyrin, and phthadocyanine." and insert -- tetrasulfonate, hematoporphyrin, and phthalocyanine. --, therefor.

In Column 52, Claim 77, Lines 59-60, delete "speciesor" and insert -- species or --, therefor.

In Column 53, Claim 84, Line 26, delete "LaC$^1$$_3$," and insert -- LaCl$_3$, --, therefor.

In Column 53, Claim 84, Line 29, delete "1($_2$0, Pb0," and insert -- K$_2$O, PbO, --, therefor.

In Column 53, Claim 90, Line 60, delete "LaCl$_3$," and insert -- LaCl$_3$, --, therefor.

In Column 54, Claim 96, Lines 22-23, delete "ablasion," and insert -- ablation, --, therefor.

In Column 54, Claim 96, Line 25, delete "hopecia" and insert -- alopecia --, therefor.

In Column 54, Claim 99, Line 58, delete "tetrasulonate, hematophorphyrin, and phthadocyanine." and insert -- tetrasulfonate, hematoporphyrin, and phthalocyanine. --, therefor.